US010653796B2

(12) United States Patent
Uhl et al.

(10) Patent No.: US 10,653,796 B2
(45) Date of Patent: May 19, 2020

(54) LIPOSOMES CONTAINING CELL PENETRATING PEPTIDES AND TETRAETHERLIPIDS FOR THE ORAL DELIVERY OF MACROMOLECULES

(71) Applicant: Universität Heidelberg, Heidelberg (DE)

(72) Inventors: Philipp Uhl, Heidleberg (DE); Max Sauter, Heidleberg (DE); Uwe Haberkorn, Schwetzingen (DE); Walter Mier, Bensheim (DE); Gert Fricker, Dossenheim (DE)

(73) Assignee: Universität Heidelberg, Heidelberg (DE)

( * ) Notice: Subject to any disclaimer, the term of this patent is extended or adjusted under 35 U.S.C. 154(b) by 0 days.

(21) Appl. No.: 15/769,630

(22) PCT Filed: Oct. 11, 2016

(86) PCT No.: PCT/EP2016/001682
§ 371 (c)(1),
(2) Date: Apr. 19, 2018

(87) PCT Pub. No.: WO2017/067642
PCT Pub. Date: Apr. 27, 2017

(65) Prior Publication Data
US 2018/0303956 A1    Oct. 25, 2018

(30) Foreign Application Priority Data
Oct. 21, 2015 (EP) .................................. 15003011

(51) Int. Cl.
*A61K 47/69*    (2017.01)
*A61K 38/14*    (2006.01)
(Continued)

(52) U.S. Cl.
CPC ........ *A61K 47/6911* (2017.08); *A61K 9/0053* (2013.01); *A61K 9/10* (2013.01);
(Continued)

(58) Field of Classification Search
CPC .... A61K 9/127; A61K 47/6911; A61K 47/42; A61K 9/19; A61K 47/26; A61K 9/10;
(Continued)

(56) References Cited

U.S. PATENT DOCUMENTS 6,120,798 A * 9/2000 Allen .................... A61K 9/1272
424/450
6,403,117 B1 * 6/2002 Sprott .................. A61K 9/1272
424/1.21
(Continued)

FOREIGN PATENT DOCUMENTS

CN    101744768    *  6/2010
WO    2010/054326    *  5/2010

OTHER PUBLICATIONS

Tseng, Yun-Long et al in Molecular Pharmacology, vol. 62, # 4, 2002, pp. 864-872.*
(Continued)

*Primary Examiner* — Gollamudi S Kishore
(74) *Attorney, Agent, or Firm* — HelixIP LLP

(57) ABSTRACT

The present invention relates to liposomal compositions, comprising liposomes comprising tetraether lipids (TELs) and cell penetrating peptides (CPPs), wherein said CPPs are attached to a compound being part of the liposome's lipid double layer. The present invention further relates to uses thereof for the oral delivery of therapeutic and/or diagnostic agents.

Figure 1:
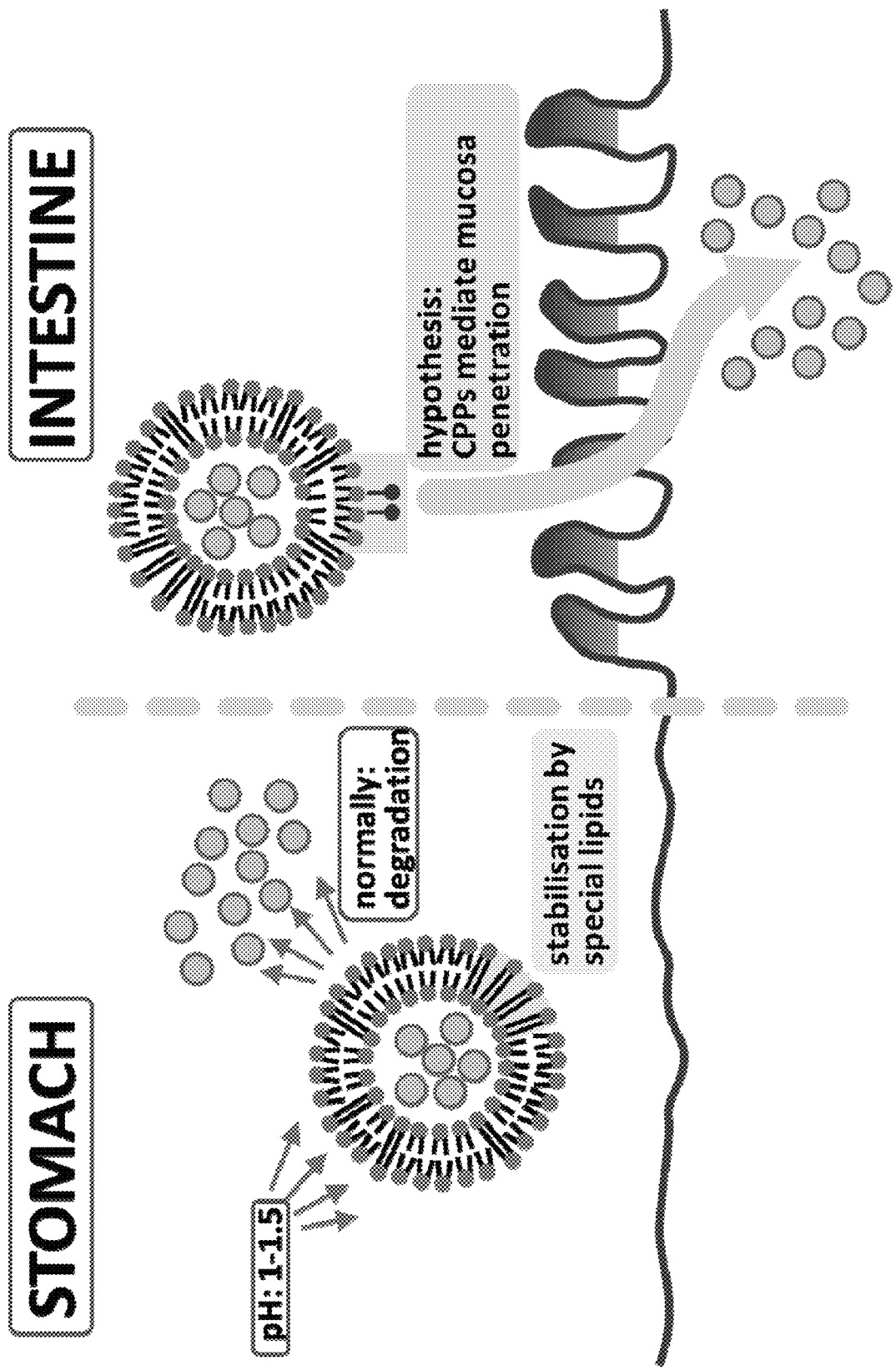

13 Claims, 25 Drawing Sheets
Specification includes a Sequence Listing.

(51) Int. Cl.
| | |
|---|---|
| *A61K 9/127* | (2006.01) |
| *A61K 9/10* | (2006.01) |
| *A61K 47/26* | (2006.01) |
| *A61K 9/19* | (2006.01) |
| *A61K 47/42* | (2017.01) |
| *A61K 47/54* | (2017.01) |
| *A61K 47/60* | (2017.01) |
| *A61K 9/00* | (2006.01) |
| *A61K 38/08* | (2019.01) |
| *A61K 38/10* | (2006.01) |

(52) U.S. Cl.
CPC .............. *A61K 9/1271* (2013.01); *A61K 9/19* (2013.01); *A61K 38/08* (2013.01); *A61K 38/10* (2013.01); *A61K 38/14* (2013.01); *A61K 47/26* (2013.01); *A61K 47/42* (2013.01); *A61K 47/544* (2017.08); *A61K 47/554* (2017.08); *A61K 47/60* (2017.08)

(58) Field of Classification Search
CPC ...... A61K 9/1271; A61K 38/14; A61K 38/10; A61K 38/08; A61K 9/0053; A61K 47/554; A61K 47/60; A61K 47/544
USPC .......................................................... 424/450
See application file for complete search history.

(56) References Cited

U.S. PATENT DOCUMENTS

| | | | | |
|---|---|---|---|---|
| 2013/0149374 A1* | 6/2013 | Lee | ...................... | A61K 9/1271 424/450 |
| 2013/0251783 A1 | 9/2013 | Parmentier et al. | | |
| 2014/0112979 A1* | 4/2014 | Andreasen | ........... | A61K 9/1277 424/450 |
| 2014/0335164 A1* | 11/2014 | Cavaco Paulo | .... | A61K 47/6911 424/450 |
| 2015/0216800 A1* | 8/2015 | Huang | ................... | A61K 33/00 424/450 |

OTHER PUBLICATIONS

Parmentier et al, Oral peptide delivery by tetraether lipid liposomes, 2011, Intl J Pharmaceutics vol. 415, pp. 150-157.

Sawant et al., Therapeutic delivery using cell-penetrating peptides CPPs: Tools for crossing the cell membrane and molecular mechanism, 2013, Eur J Nanomed vol. 5, pp. 141-158.

Qin et al, Liposome formulated with TAT-modified cholesterol for improving brain delivery and therapeutic efficacy on . . . , 2011, Int J Pharmaceut vol. 420, pp. 304-312.

Zhang et al., Hepatitis B virus preS1-derived lipopeptide functionalized liposomes for targeting hepatic cells, 2014, Biomaterials vol. 23, pp. 6130-6141.

Chen et al., Effect of cell-penetrating peptide-coated nanostructured lipid carriers on the oral absorption of tripterine, 2012, Int'l J Nanomedicine vol. 7, pp. 4581-4591.

Fan et al., Design and evaluation of solid lipid nanoparticles modified with peptide ligand for oral delivery of . . . , 2014, Eur J Pharmaceut Biopharm vol. 88, pp. 518-528.

Fu et al, Tumor-targeted paclitaxel delivery and enhanced penetration using TAT-decorated liposomes comprising redox-responsive . . . , 2014, J. Pharma Sci vol. 103, pp. 1160-1173.

Khafagy et al, Oral biodrug delivery using cell-penetrating peptide, 2012, Advanced Drug Delivery Reviews vol. 64, pp. 531-539.

Laettig-Tuennemann et al, Backbone rigidity and static presenation of guanidinium groups increases cellular uptake of arginine rich . . . , 2011, Nature Commun vol. 2, pp. 1-6.

Nischan et al, Covalent attachment of cyclic TAT peptides to GFP results in protein delivery into live cells with immediate . . . , 2015, Ang Chemie vol. 54, pp. 1950-1953.

Parmentier et al., Oral peptide delivery by tetraether lipid liposomes, 2011, Intl J Journal of Pharmaceutics vol. 415, pp. 150-157.

\* cited by examiner

```
                          SEQUENCE LISTING

<160> NUMBER OF SEQ ID NOS: 7

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 16
<212> TYPE: PRT
<213> ORGANISM: Human immunodeficiency virus type 1

<400> SEQUENCE: 2

Cys Gly Arg Lys Lys Lys Arg Arg Gln Arg Arg Arg Pro Pro Gln Cys
1               5                   10                  15

<210> SEQ ID NO 3
<211> LENGTH: 27
<212> TYPE: PRT
<213> ORGANISM: Artificial sequence
<220> FEATURE:
<223> OTHER INFORMATION: artificially designed cell penetrating peptide

<400> SEQUENCE: 3

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 4
<211> LENGTH: 9
<212> TYPE: PRT
<213> ORGANISM: Artificial sequence
<220> FEATURE:
<223> OTHER INFORMATION: artificially designed cell penetrating peptide

<400> SEQUENCE: 4

Arg Arg Arg Arg Arg Arg Arg Arg Arg
1               5

<210> SEQ ID NO 5
<211> LENGTH: 18
<212> TYPE: PRT
<213> ORGANISM: Mus musculus
<220> FEATURE:
<221> NAME/KEY: MISC_FEATURE
<222> LOCATION: (18)..(18)
<223> OTHER INFORMATION: K-amide

<400> SEQUENCE: 5

Leu Leu Ile Ile Leu Arg Arg Arg Ile Arg Lys Gln Ala His Ala His
1               5                   10                  15

Ser Lys

<210> SEQ ID NO 6
<211> LENGTH: 28
```

```
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: L-amide

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Ile Ser Ile Leu
            20                  25

<210> SEQ ID NO 7
<211> LENGTH: 27
<212> TYPE: PRT
<213> ORGANISM: Human immunodeficiency virus

<400> SEQUENCE: 7

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

LIPOSOMES CONTAINING CELL PENETRATING PEPTIDES AND TETRAETHERLIPIDS FOR THE ORAL DELIVERY OF MACROMOLECULES

The present invention relates to liposomal compositions, comprising liposomes comprising tetraether lipids (TELs) and cell penetrating peptides (CPPs), wherein said CPPs are attached to a compound being part of the liposome's lipid double layer. The present invention further relates to uses thereof for the oral delivery of therapeutic and/or diagnostic agents.

Oral drug delivery is considered as the most advantageous way of application, in particular for the treatment of chronic diseases, which demand long-term and repeated drug administration. The oral route offers high drug safety and is widely accepted among patients due to its convenience. Additionally, non-sterility of oral drug forms reduces costs in production, storage and distribution, which could contribute to health care improvement in third world countries. It is estimated, that 90% of all marketed drug formulations are for oral use.

However, many drugs, particularly peptides and other macromolecular drugs, show both a very poor stability under the acid conditions in the stomach after oral administration and also poor absorption across the gastrointestinal barrier (FIG. 1). To overcome this problem, different approaches to improve the bioavailability have been tested in the past years including solid lipid nanoparticles, nano- or micro-emulsions, or liposomes. However, conventional liposomal formulations have not been very convincing due to their instability in the gastrointestinal tract (GIT).

A significant improvement in liposomes can be made by the combination of conventional phospholipids (PLs) and so-called tetraether lipids, specific lipids derived from archaea, e.g. the extremophilic archaeon *Sulfolobus acidocaldarius*. Recent studies showed that these TELs can both improve the liposomal stability in the GIT and also mediate mucosal penetration.

*S. acidocaldarius* grows at temperatures between 50 to 100° C. mostly under acidic conditions, making a stable cell membrane inevitable. Archaeal membrane lipids comprise mainly $C_{20}$-$C_{40}$ isoprenoid-subunit backbones, linked by ether bonds to glycerol and/or nonitol bridge group(s). The bridge group is either unsubstituted or substituted with one of a wide variety of polar or nonpolar head groups. The quantity of these moieties in the archaeal cell membrane differs with growth conditions and increases with the environmental temperature. The TELs glycerylcalditytetraether (GCTE) and diglyceryltetraether (DGTE) with an average number of four to six cyclopentyl rings can be isolated from *S. acidocaldarius*.

However, even when using TELs, the mucosal penetration of said liposomes is still unsatisfactory in many cases. Thus, there is still a need for improving the mucosal penetration of liposomes.

In view of the above, the technical problem underlying the present invention is the provision of means for the delivery of drugs via the oral route, having enhanced mucosal penetration.

The solution to the above technical problem is achieved by the embodiments characterized in the claims.

In particular, in a first aspect, the present invention relates to a liposomal composition comprising liposomes, said liposomes comprising (a) tetraether lipids (TELs), and
(b) cell penetrating peptides (CPPs), wherein said CPPs are attached to a compound being part of the liposome's lipid double layer.

As used herein, the term "liposomal composition" relates to a composition comprising liposomes. The term "liposome" as used herein refers to artificially prepared vesicles composed of lipid bilayers. Liposomes can be used for delivery of agents due to their unique property of encapsulating a region of aqueous solution inside a hydrophobic membrane. Dissolved hydrophilic solutes cannot readily pass through the lipid bilayer. Hydrophobic compounds can be dissolved in the lipid bilayer, and in this way liposomes can carry both hydrophobic and hydrophilic compounds. To deliver the molecules to sites of action, the lipid bilayer can fuse with other bilayers such as cell membranes, thus delivering the liposome contents. By making liposomes in a solution of an agent, it can be delivered to the inner lumen of the liposome.

TELs that can be used for the formation of liposomes are not particularly limited and are known in the art. In particular embodiments, said TELs are derived from an archaeal species of the genus *Sulfolobus*, e.g. *S. islandicus* or *S. acidocaldarius*, wherein the latter is particularly preferred. In a preferred embodiment, the TELs are selected from the group consisting of glycerylcalditytetraether (GCTE), diglyceryltetraether (DGTE), and combinations thereof.

Preferably, the liposomes used in the compositions of the present invention comprise said TELs in an amount of 1 to 25 mol-%, preferably 1 to 10 mol-%, more preferably 3 to 7 mol-%, more preferably 4 to 6 mol-% based on the total lipid amount. In specific embodiments, said liposomes comprise said TELs in an amount of about 5 mol-% based on the total lipid amount.

Besides the presence of TELs as described above, the liposomes used in the compositions according to the present invention are not particularly limited to specific lipids. In particular, the lipids used for the generation of said liposomes can be any suitable lipids known in the art. These lipids include—but are not restricted to—cholesterol or derivatives thereof, phospholipids, lysophospholipids or further tetraetherlipids. Accordingly, in a preferred embodiment, said liposomes comprise one or more lipids, selected from the group consisting of cholesterol and derivatives thereof, phospholipids, lysophospholipids, and tetraetherlipids. Preferred cholesterol derivatives in the context of the present invention are steroids and compounds having a basic steroid molecular structure. Preferably, said liposomes comprise phospholipids, wherein said phospholipids can be synthetic, semi-synthetic or natural phospholipids. In general, suitable lipids can be selected from the group consisting of phosphatidylcholines, phosphatidylethanolamines, phosphatidylinosites, phosphatidylserines, cephalines, phosphatidylglycerols, and lysophospholipids. In a particular embodiment of the present invention, the liposomes comprise egg phosphatidylcholine (E-PC; lecithin) and cholesterol, preferably in an amount of about 85 mol-% E-PC and about 10 mol-% cholesterol. The liposomes to be used according to the present invention may further comprise any further suitable agents such as e.g. enzyme inhibitors, permeation enhancers, or other lipophilic or hydrophilic substances that can be used for the stabilization of liposomes or for altering liposome properties. Such lipophilic or hydrophilic substances are not particularly limited and are known in the art. They include for example vitamin E, fatty acids, waxes, and mono-, di- and triglycerides. Furthermore, substances that enhance the bioavailability of enclosed active agents, like enzyme inhibitors, tight junction modulators or chelating agents can be added.

CPPs that can be used in connection with the present invention are not particularly limited and are known in the art. Preferably, the CPPs are CPPs having a positive total charge. Respective CPPs are known in the art. More preferably, the CPPs are selected from the group consisting of linear or cyclized penetratin (SEQ ID NO: 1; RQIKIWFQN-RRMKWKK), derived from *Drosophila melanogaster*, TAT (transactivator of transcription)-peptide (SEQ ID NO: 2; CGRKKKRRQRRRPPQC), derived from HIV-1, MAP (model amphiphatic peptide) (SEQ ID NO: 3; GALFLG-FLGAAGSTMGAWSQPKSKRKV), which is an artificial peptide, R9 (SEQ ID NO: 4; RRRRRRRRR), which is an artificial peptide, pVEC (SEQ ID NO: 5; LLIILRR-RIRKQAHAHSK-amide), which is a CPP derived from murine vascular endothelial cadherin, transportan (SEQ ID NO: 6; GWTLNSAGYLLGKINLKALAALAKISIL-amide), which is derived from the human neuropeptide galanin, and MPG (SEQ ID NO: 7; GALFLGFLGAAGST-MGAWSQPKSKRKV), which is derived from HIV, combinations thereof, and dimers thereof. In this context, all of the above peptides can be present in a linear or in a cyclized form, wherein the cyclized form is preferred. Further, the CPPs of the present invention can be composed of L-amino acids, D-amino acids, or mixtures thereof, wherein for linear CPPs, D-amino acids are preferred.

According to the present invention, CPPs are attached to a compound being part of the liposome's lipid double layer. In this context, the term "being part of the liposome's lipid double layer" is intended to indicate the fact that said phospholipid is integrated into said lipid double layer. Preferably, attachment is covalent attachment. The compound to which the CPPs are attached and which is part of the liposome's lipid double layer is preferably a suitable lipid as defined above, e.g. a lipid selected from the group consisting of cholesterol and derivatives thereof, phospholipids, lysophospholipids, and tetraetherlipids, wherein phospholipids are preferred, and wherein said lipids can be modified and/or activated lipids. Preferably, the CPPs are attached to said compound via a linker. In this context, monomeric CPPs can be covalently attached to a phospholipid via a linker (FIG. 3), or dimerized CPPs, wherein homo- and heterodimers are possible, are covalently attached to a phospholipid via a linker (FIG. 4). Dimerization of CPPs can be effected by any means known in the art. In a particular embodiment, CPPs are dimerized via the tripeptide KAK. However, attachment is also possible without a linker, e.g. when using modified and/or activated lipids, such as e.g. phospholipids with a maleimide-modified headgroup.

Preferably, the liposomes comprised in the liposomal compositions of the present invention comprise said CPPs in an amount of 0.05 to 5 mol-%, preferably 0.1 to 1 mol-%, based on the total lipid amount. In the case of monomeric CPPs, these are preferably comprised in an amount of 0.05 to 2 mol-%, preferably 0.1 to 1 mol-%, based on the total lipid amount. In the case of dimerized CPPs, these are preferably comprised in an amount of 0.05 to 0.5 mol-%, preferably 0.1 mol-%, based on the total lipid amount.

Suitable phospholipids for the covalent attachment of CPPs are not particularly limited to specific phospholipids. In particular, the phospholipids used for the covalent attachment of CPPs can be any suitable phospholipids known in the art, wherein said phospholipids can be synthetic, semisynthetic or natural phospholipids. In general, suitable phospholipids can be selected from the group consisting of phosphatidylcholines, phosphatidylethanolamines, phosphatidylinosites, phosphatidylserines, cephalines, phosphatidylglycerols, and lysophospholipids. A particular phospholipid in this respect is egg phosphatidylcholine (E-PC; lecithin). Further, suitable phospholipids in this respect include PEG-modified versions of the above phospholipids, e.g. DSPE-PEG(2000) Maleimide (1,2-distearoyl-sn-glycero-3-phosphoethanolamine-N-[maleimide (polyethylene glycol)-2000] (ammonium salt)).

Suitable linkers for the covalent attachment of CPPs to phospholipids are not particularly limited and are known in the art. They include for example bifunctional PEG-linkers in general; e.g. SM(PEG)$_{24}$ (PEGylated, long-chain SMCC crosslinker). Particular exemplary linkers in this respect are SMCC (succinimidyl-4-(N-maleimidomethyl)cyclohexane-1-carboxylate)-linker, and 6-maleimido hexanoic acid linker. In this context, the length of the PEG moiety in such linkers influences the encapsulation efficiency of drugs that are incorporated into the liposomes comprised in the liposomal compositions of the present invention. Accordingly, said PEG moiety preferably has a length of 8 to 50 individual PEG units. Further, methods for covalently linking CPPs to phospholipids via linkers are not particularly limited and are known in the art.

The lipids used for preparation of the liposomes comprised in the composition of the present invention can also be attached to target seeking structures such as peptide sequences, antibodies, receptor ligands and surfactants.

In a preferred embodiment, the liposomes comprised in the composition of the present invention exhibit a Z-Average measured by dynamic light scattering after dilution in aqueous medium of at most 350 nm and a polydispersity index (PDI) of at most 0.3, where a Z-Average of 100 to 200 nm and a polydispersity index of 0.1 to 0.3, preferably about 0.2 is particularly preferred.

Methods for the generation of liposomes are not particularly limited and are known in the art. They include for example high pressure homogenization, extrusion and dual asymmetric centrifugation (DAC).

In preferred embodiments, the liposomal compositions of the present invention can further comprise at least one additional therapeutic agent and/or at least one diagnostic agent.

Respective therapeutic agents are not particularly limited and include any agents for which oral delivery might be interesting. They include for example macromolecules such as peptidic drugs (e.g. octreotide, glatiramer acetate, vancomycin, Myrcludex B, all sorts of insulin, and liraglutide, as well as other GLP (glucagon-like peptide)-analogues such as exenatide, lixisenatide, albiglutide, dulaglutide, taspoglutide, and semaglutide), and proteins or antibodies (e.g. etanercept; pegfilgrastim; adalimumab, infliximab, rituximab, epoietin alfa, tratuzumab, ranibizumab, beta-interferon, omalizumab). Other examples include pharmaceutically active agents selected from the group consisting of human growth hormone, growth hormone releasing hormone, growth hormone releasing peptide, interferons, colony stimulating factors, interleukins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin and fragment polypeptides thereof, apolipoprotein-E, erythropoietin, factor VII, factor VIII, factor IX, plasminogen activating factor, urokinase, streptokinase, protein C, C-reactive protein, renin inhibitor, collagenase inhibitor, superoxide dismutase, platelet-derived growth factor, epidermal growth factor, osteogenic growth factor, bone stimulating protein, calcitonin, insulin, atriopeptin, cartilage inducing factor, connective tissue activating factor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, monoclonal or polyclonal antibodies against various viruses, bacteria, or toxins, virus-derived vaccine antigens, octreotide, cyclosporine, rifampycin, lopinavir, ritonavir, vancomycin, telavancin, oritavancin, dalbavancin, bisphosphonates, itraconazole, danazol, paclitaxel, cyclosporin, naproxen, capsaicin, albuterol sulfate, terbutaline sulfate, diphenhydramine hydrochloride, chlorpheniramine maleate, loratidine hydrochloride, fexofenadine hydrochloride, phenylbutazone, nifedipine, carbamazepine, naproxen, cyclosporin, betamethosone, danazol, dexamethasone, prednisone, hydrocortisone, 17 beta-estradiol, ketoconazole, mefenamic acid, beclomethasone, alprazolam, midazolam, miconazole, ibuprofen, ketoprofen, prednisolone, methylprednisone, phenytoin, testosterone, flunisolide, diflunisal, budesonide, fluticasone, insulin, glucagon-like peptide, C-Peptide, erythropoietin, calcitonin, lutenizing hormone, prolactin, adrenocorticotropic hormone, leuprolide, interferon alpha-2b, interferon beta-1a, sargramostim, aldesleukin, interferon alpha-2a, interferon alpha-n3alpha-proteinase inhibitor, etidronate, nafarelin, chorionic gonadotropin, prostaglandin E2, epoprostenol, acarbose, metformin, desmopressin, cyclodextrin, antibiotics, antifungal drugs, steroids, anticancer drugs, analgesics, anti-inflammatory agents, anthelmintics, anti-arrhythmic agents, penicillins, anticoagulants, antidepressants, antidiabetic agents, antiepileptics, antihistamines, antihypertensive agents, antimuscarinic agents, antimycobacterial agents, antineoplastic agents, CNS-active agents, immunosuppressants, antithyroid agents, antiviral agents, anxiolytic sedatives, hypnotics, neuroleptics, astringents, beta-adrenoceptor blocking agents, blood products and substitutes, cardiacinotropic agents, contrast media, corticosteroids, cough suppressants, expectorants, mucolytics, diuretics, dopaminergics, antiparkinsonian agents, haemostatics, immunological agents, lipid regulating agents, muscle relaxants, parasympathomimetics, parathyroid calcitonin, prostaglandins, radiopharmaceuticals, sex hormones, steroids, anti-allergic agents, stimulants, anoretics, sympathomimetics, thyroid agents, vasidilators, xanthines, heparins, therapeutic oligonucleotides, somatostatins and analogues thereof, and pharmacologically acceptable organic and inorganic salts or metal complexes thereof.

Further, respective diagnostic agents are not particularly limited and include any agents for which oral delivery might be interesting.

The above agents may be present in the liposomal compositions of the present invention enclosed in the liposomes, i.e., in the inner lumen of said liposomes, e.g. when said agents are hydrophilic, or integrated into the liposomal membrane, e.g. when said agents are lipophilic. In this context, the encapsulation of therapeutic and/or diagnostic agents depends on the hydrophilicity of said agents and the liposome preparation method.

In a preferred embodiment, the content of therapeutic and/or diagnostic agent in the liposomal compositions according to the present invention is above 0 and at most 50% (w/w) in regard to the used amount of agent.

In accordance with the above aspect, the liposomal compositions of the present invention can be for use in medicine. Preferably, said liposomal compositions are for use in the treatment of sepsis, diabetes, rheumatism, acromegaly, all kinds of hepatitis, all kinds of cancer, and anemia. Preferably, the liposomal compositions for use of the present invention are for oral administration.

Recent studies showed that pretreatment with the proton pump inhibitor omeprazole decreases the diffusion of protons into liposomes and, as a consequence, decreases the denaturation of the encapsulated agents such as proteins by raising the pH in the stomach. Accordingly, in a preferred embodiment of the liposomal compositions for use according to the present invention, the subject is pretreated with a proton pump inhibitor, wherein said proton pump inhibitor is preferably omeprazole (6-methoxy-2-[(4-methoxy-3,5-dimethylpyridin-2-yl)methanesulfinyl]-1H-1,3-benzodiazole), pantoprazole ((RS)-6-(difluoromethoxy)-2-[(3,4-dimethoxypyridin-2-yl)methylsulfinyl]-1H-benzo[d]imidazole), esomeprazole ((S)-5-methoxy-2-[(4-methoxy-3,5-dimethyl-pyridin-2-yl)methylsulfinyl]-3H-benzoimidazole), lansoprazole ((RS)-2-([3-methyl-4-(2,2,2-trifluoroethoxy)pyridin-2-yl]methylsulfinyl)-1H-benzo[d]imidazole), and/or rabeprazole ((RS)-2-([4-(3-methoxypropoxy)-3-methylpyridin-2-yl]methylsulfinyl)-1H-benzo[d]imidazole).

Advantageously, the liposomal compositions of the present invention can be freeze-dried, e.g. using 300 to 500 mM sucrose as a lyoprotector, which enables the long-term storage of said compositions.

In a related second aspect, the present invention relates to the use of a liposomal composition of the present invention for the oral delivery of at least one therapeutic agent and/or at least one diagnostic agent.

In this context, the term "oral delivery" relates to the delivery of one or more agents by way of oral administration of said agents.

In this aspect, all relevant limitations and definitions provided for the first aspect of the present invention apply in an analogous manner. In particular, the liposomal compositions, therapeutic agents, and diagnostic agents are as defined above.

In a further related aspect, the present invention relates to a method of delivering at least one therapeutic agent and/or at least one diagnostic agent to a subject, comprising the step of administering, preferably orally administering, a liposomal composition of the present invention to said subject.

In this aspect, all relevant limitations and definitions provided for the first aspect of the present invention apply in an analogous manner. In particular, the liposomal compositions, therapeutic agents, and diagnostic agents are as defined above.

As used herein, the term "about" is intended to be a modifier of ±10% of the specified value. As an example, the term "about 5%" is intended to encompass the range of 4.5 to 5.5%.

The terms "comprising/comprises", "consisting of/consists of", and "consisting essentially of/consists essentially of" are used herein in an interchangeable manner, i.e., each of said terms can expressly be exchanged against one of the other two terms.

The terms "composition" and "formulation" are used herein in an equivalent manner and are expressly intended to be interchangeable with one another.

Figure 2:
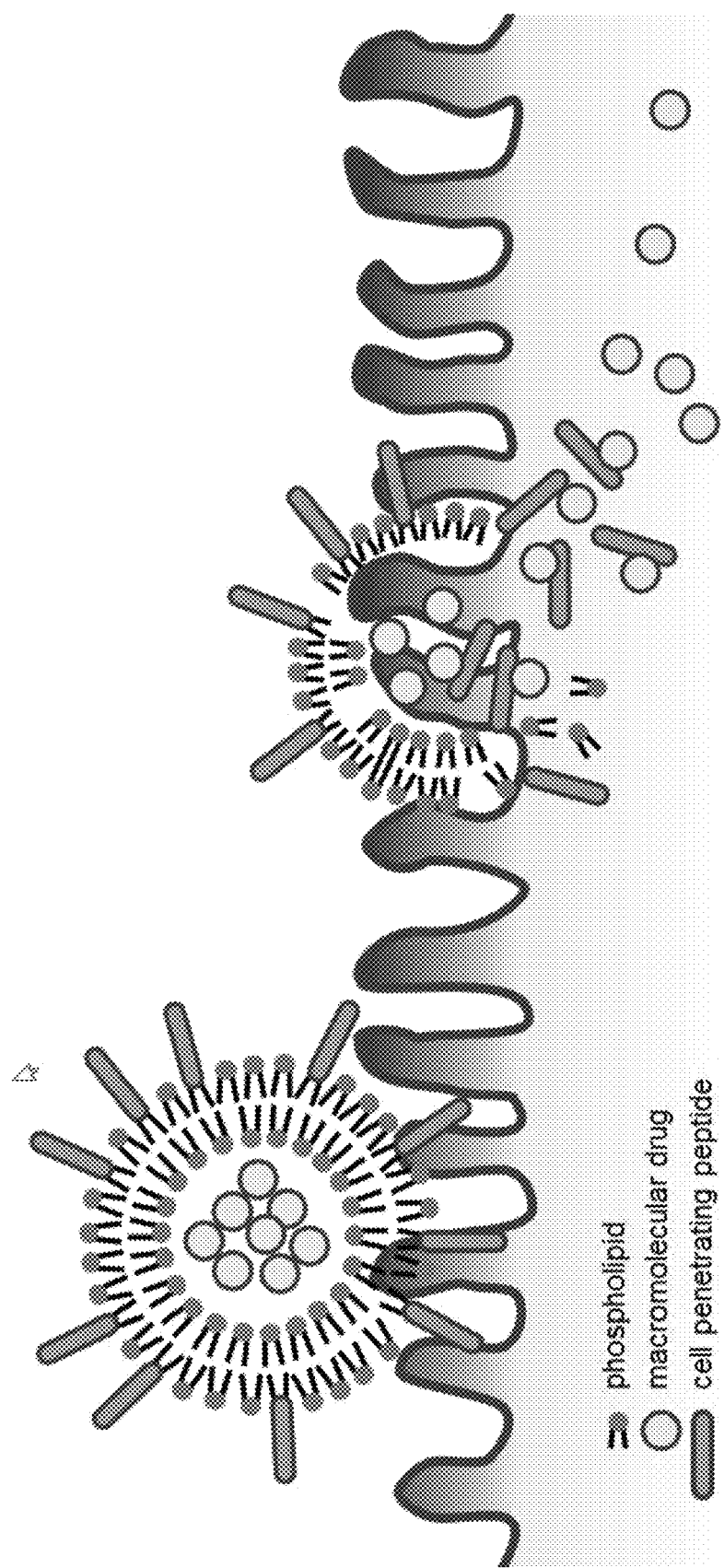

The present invention utilizes CPPs that are covalently attached to liposomes for advantageously increasing mucosal penetration of said liposomes (FIG. 2).

The figures show:

FIG. 1:
Degradation in the stomach and poor mucosa penetration are the main hurdles that prevent the oral availability of biologicals. Using TEL-liposomes comprising CPPs, both hurdles can be overcome.

FIG. 2:
Liposomes containing CPPs coupled to phospholipids are shown. The CPPs enhance the mucosa penetration of macromolecular drugs incorporated into the liposomes.

Figure 3:
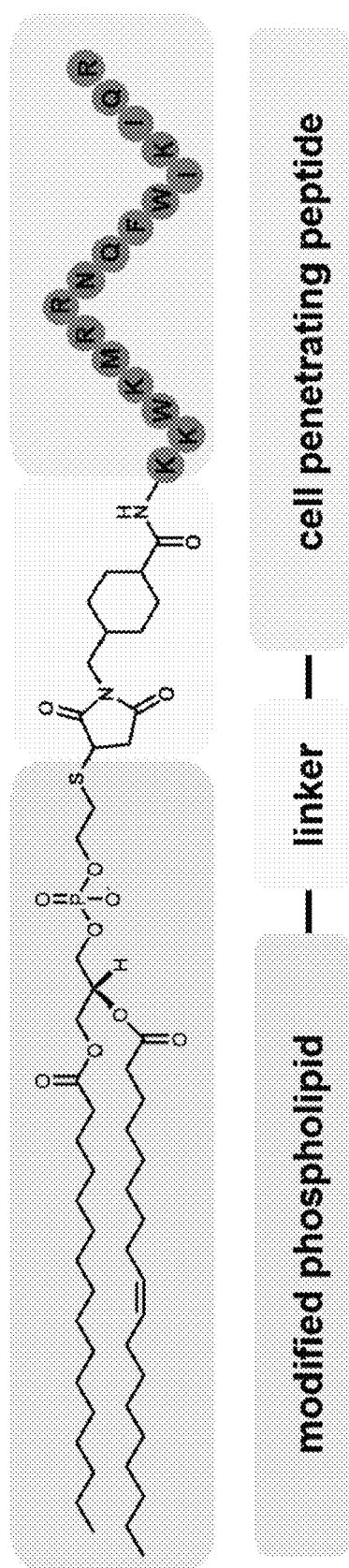
Figure 4:
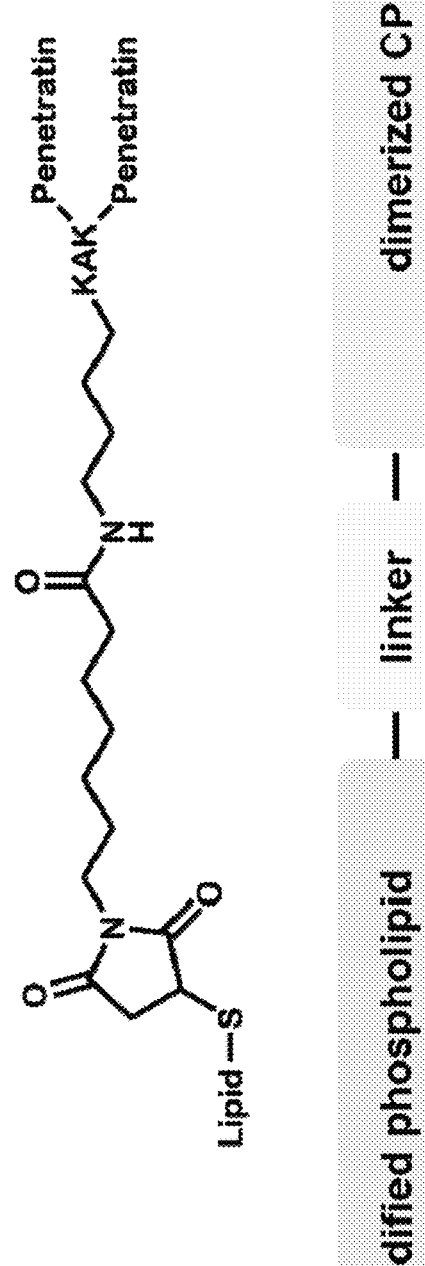

FIG. 3:
The structure of a phospholipid modified with a monomeric CPP is shown. The CPP is the naturally occurring peptide penetratin, the linker is an SMCC-linker.

FIG. 4:
The structure of a phospholipid modified with dimerized CPPs is shown. The CPP is the naturally occurring peptide penetratin, wherein two penetratin molecules are dimerized via the tripeptide KAK. The linker is a 6-maleimido hexanoic acid linker.

Figure 5:
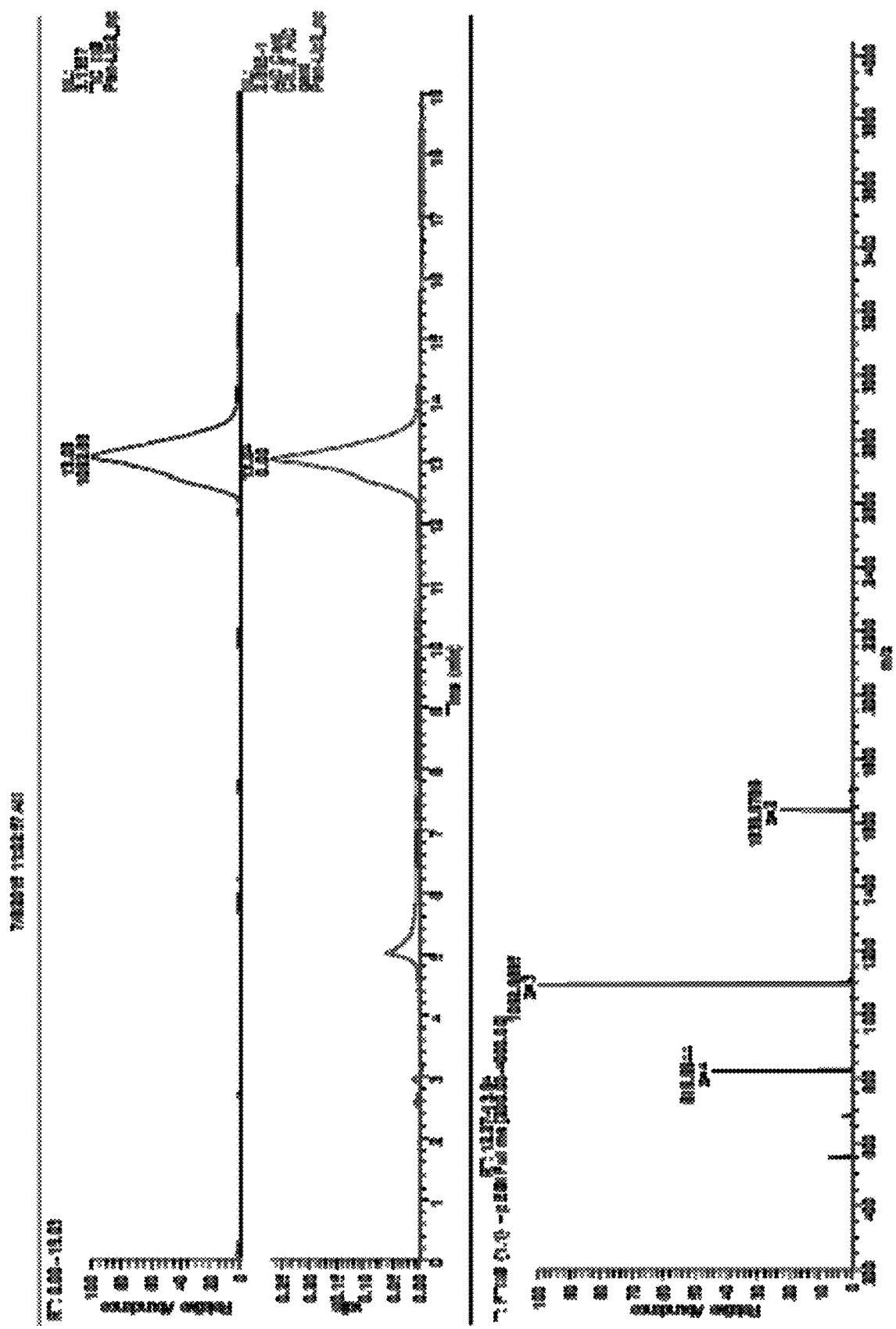

FIG. 5:
Analysis of the Penetratin-lecithin-conjugate by mass spectrometry.

Figure 6:
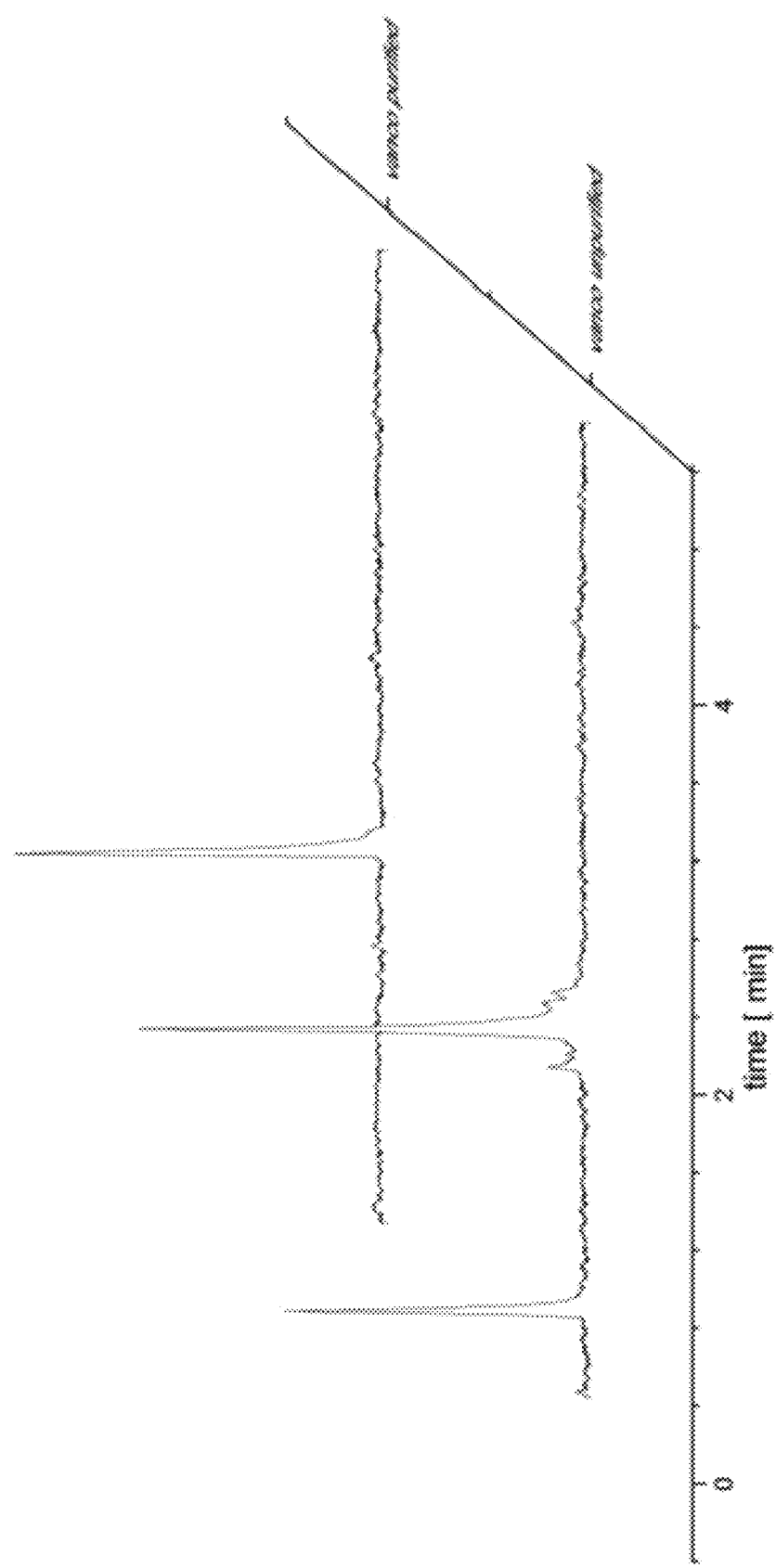

FIG. 6:
RadioHPLC spectra of $^{131}$I radiolabeled vancomycin before/after purification by preparative radioHPLC.

Figure 7:
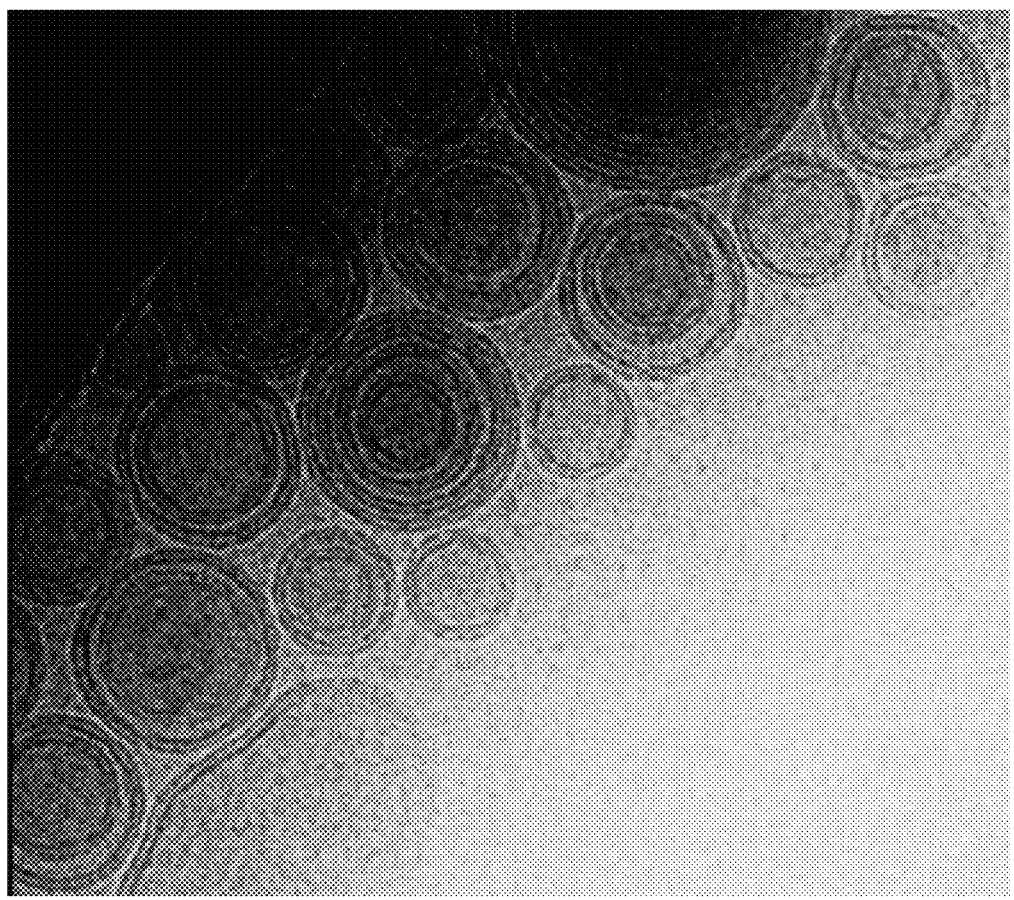

FIG. 7:
Kryo-EM micrograph of the CPP-TEL-vancomycin-liposomes.

Figure 8:
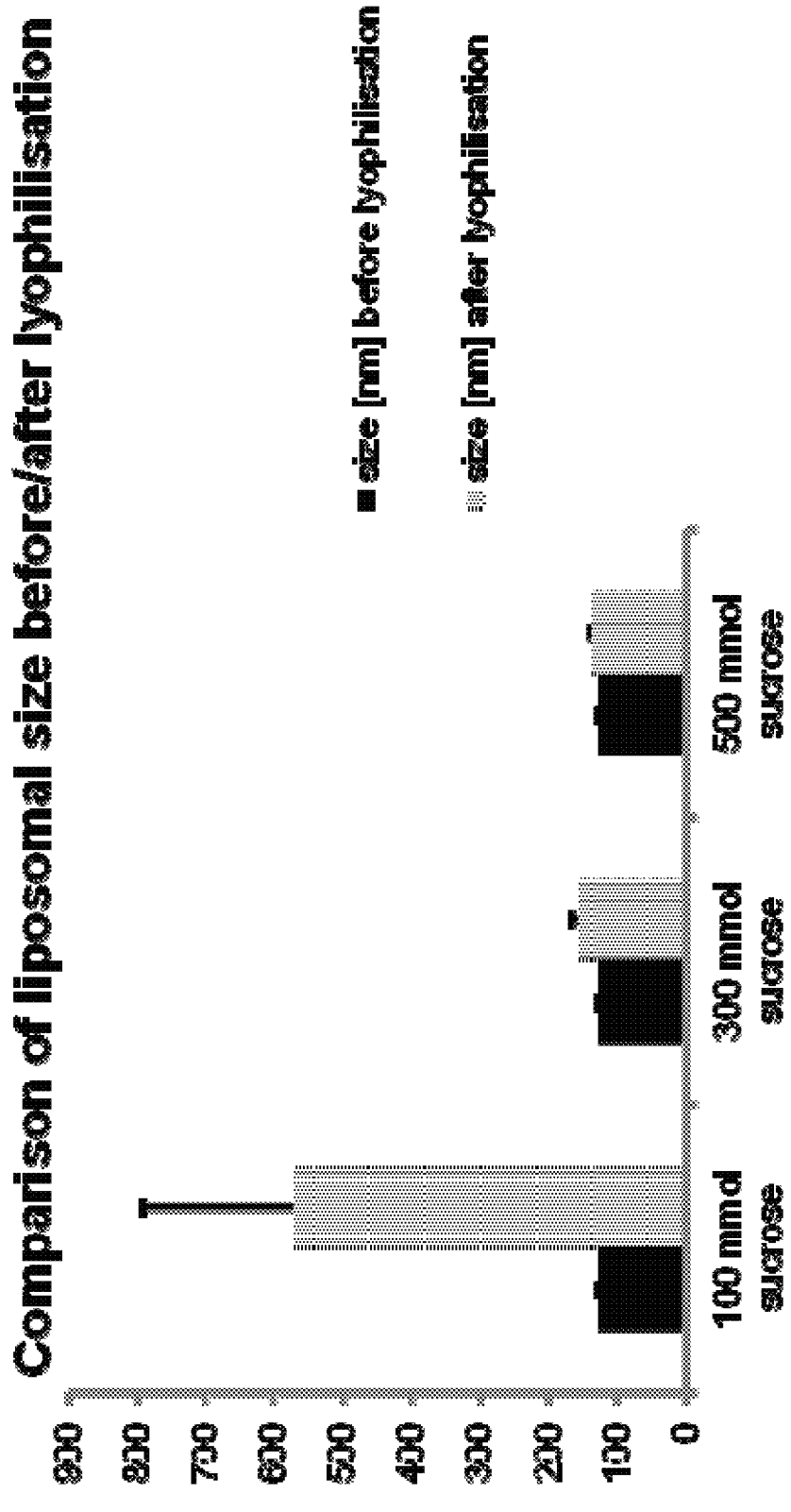
Figure 8:
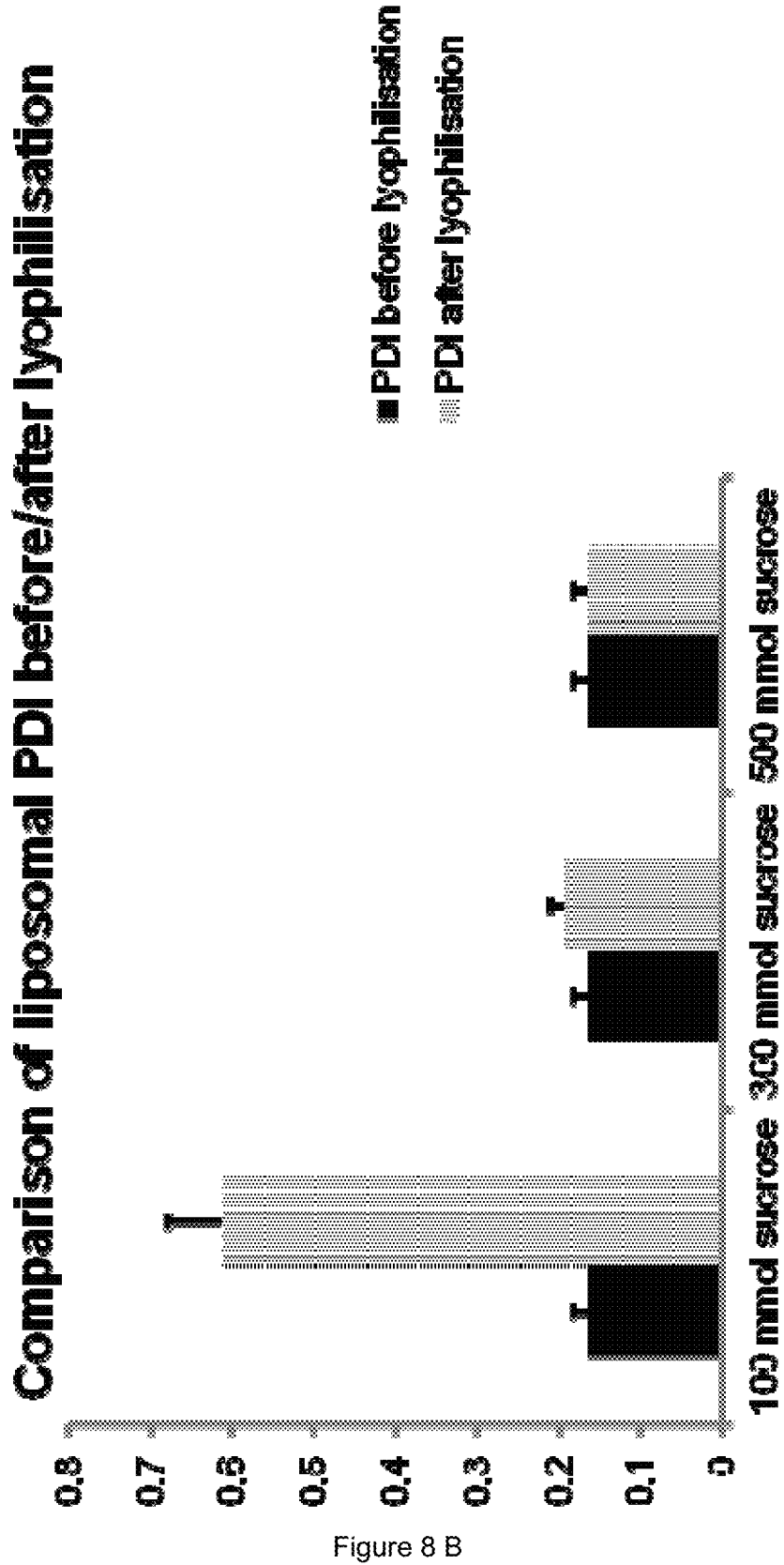

FIG. 8:
(A) Comparison of liposomal size and (B) liposomal PDI before/after the freeze drying process using 100-500 mM Sucrose as lyoprotector.

Figure 9:
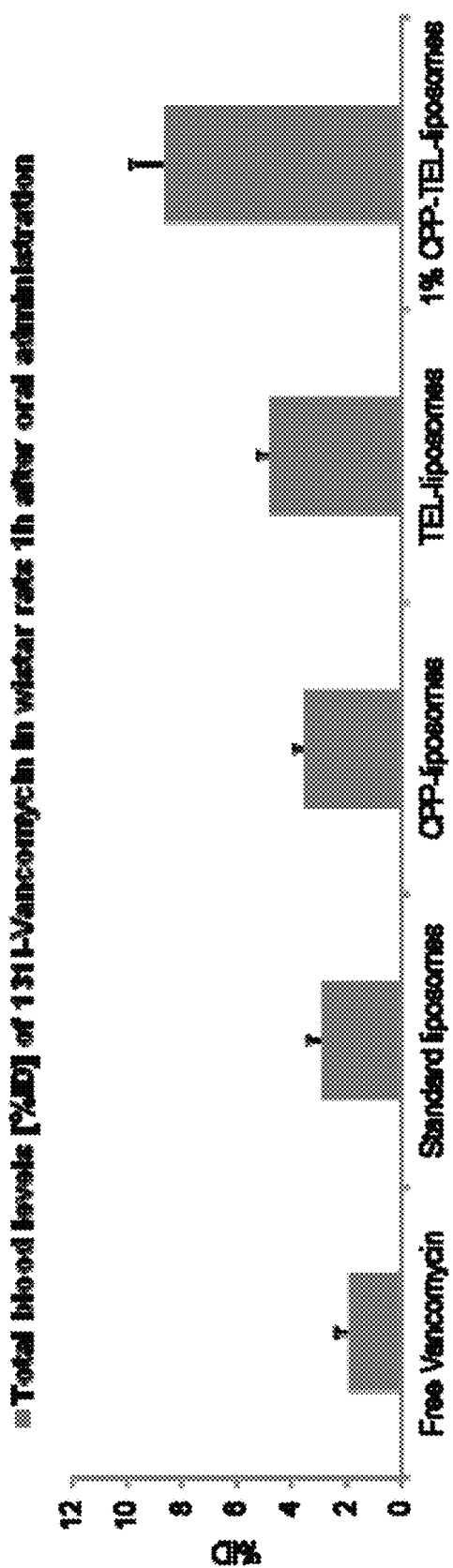

FIG. 9:
Comparison of blood levels of $^{131}$I-Vancomycin 1 h after oral administration.

Figure 10:
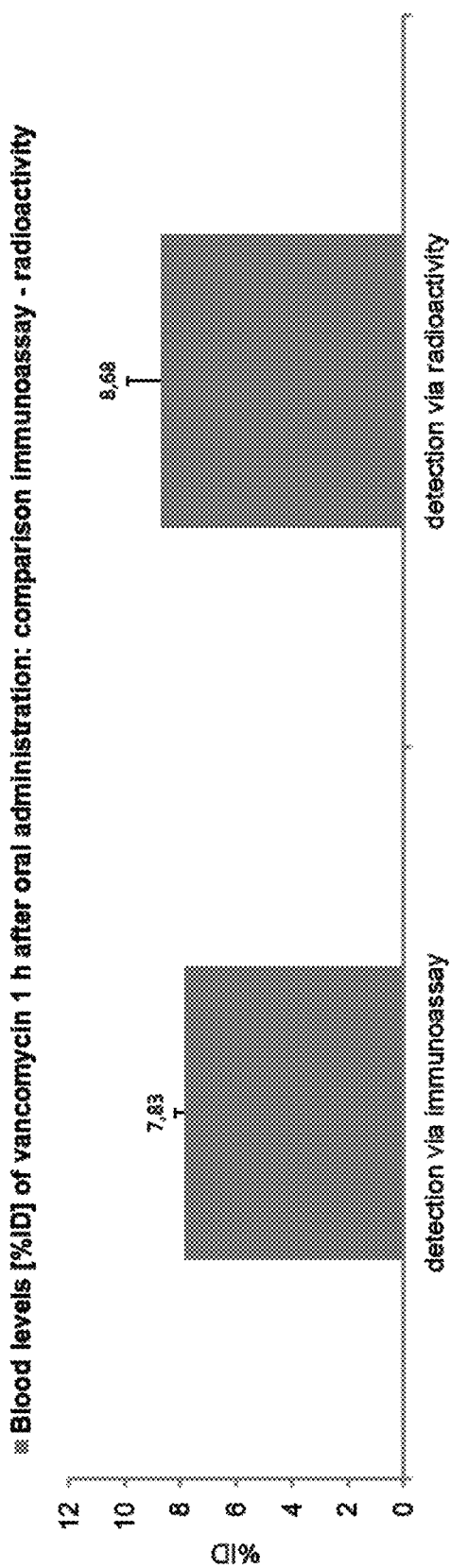

FIG. 10:
Comparison of the CPP-TEL-liposomal blood levels.

Figure 11:
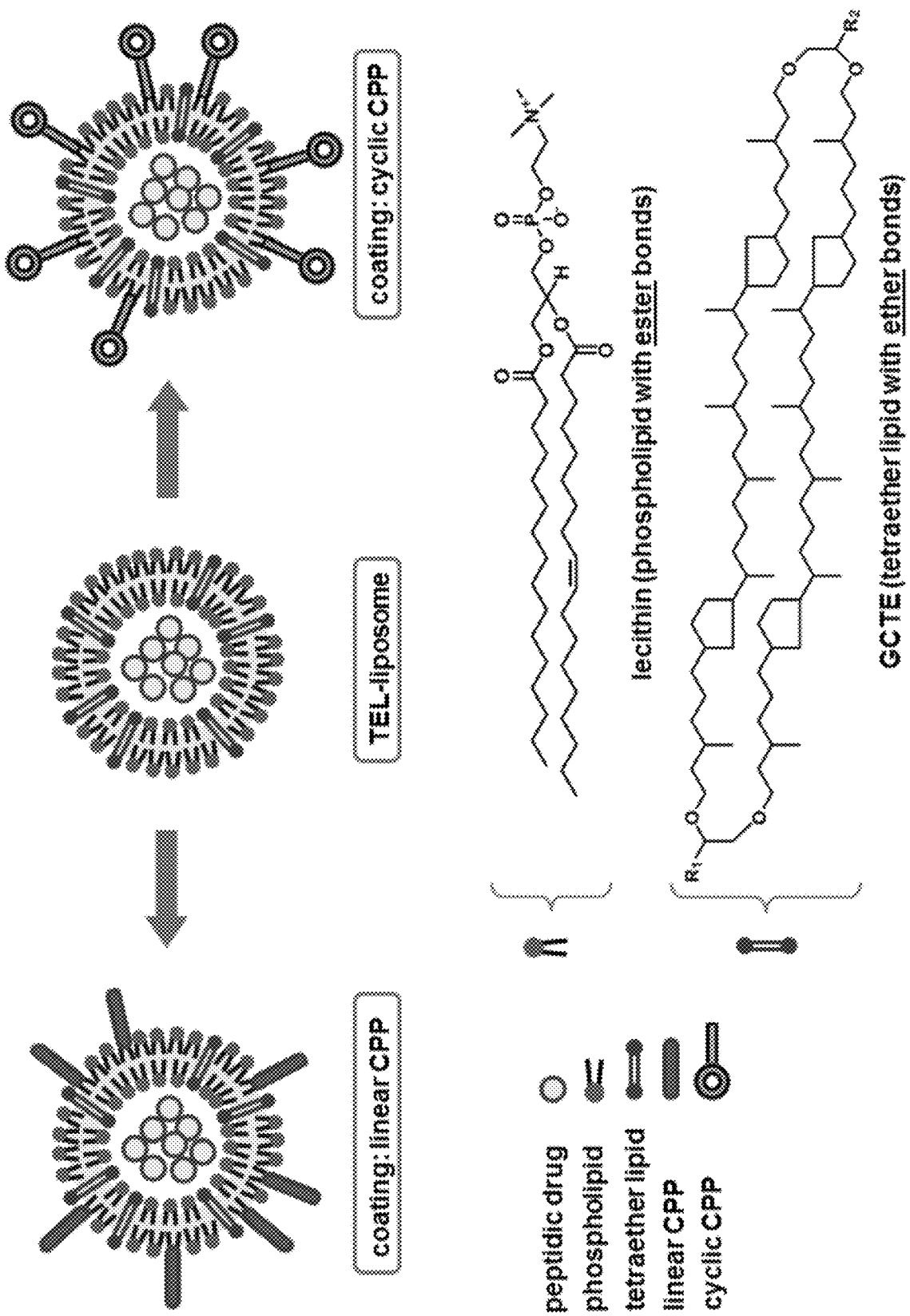

FIG. 11:
The novel liposomes contain specific tetraether lipids and CPP-phospholipid-conjugates (linear and cyclic).

Figure 12:
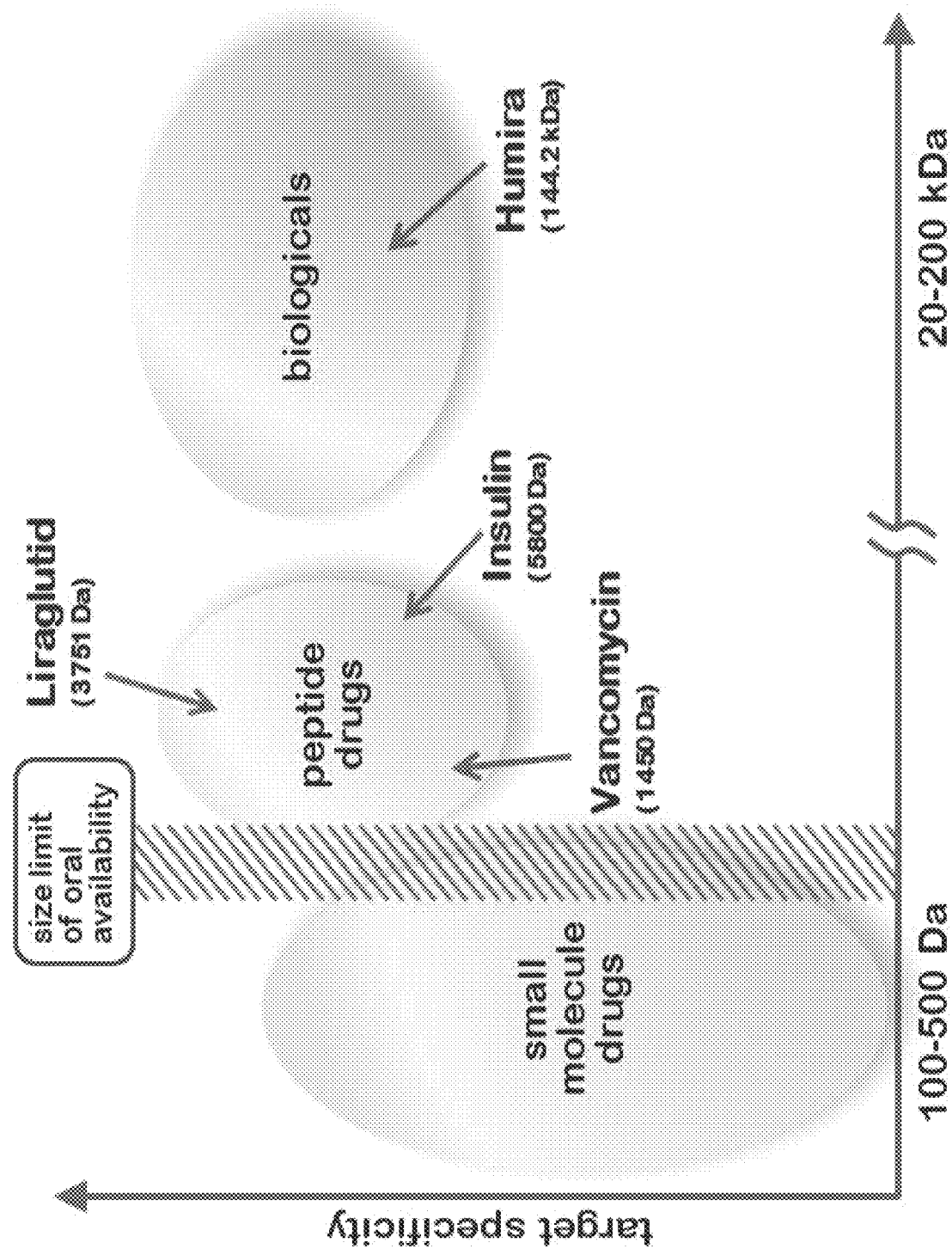

FIG. 12:
Model substances and molecular weight for oral drug delivery.

Figure 13:
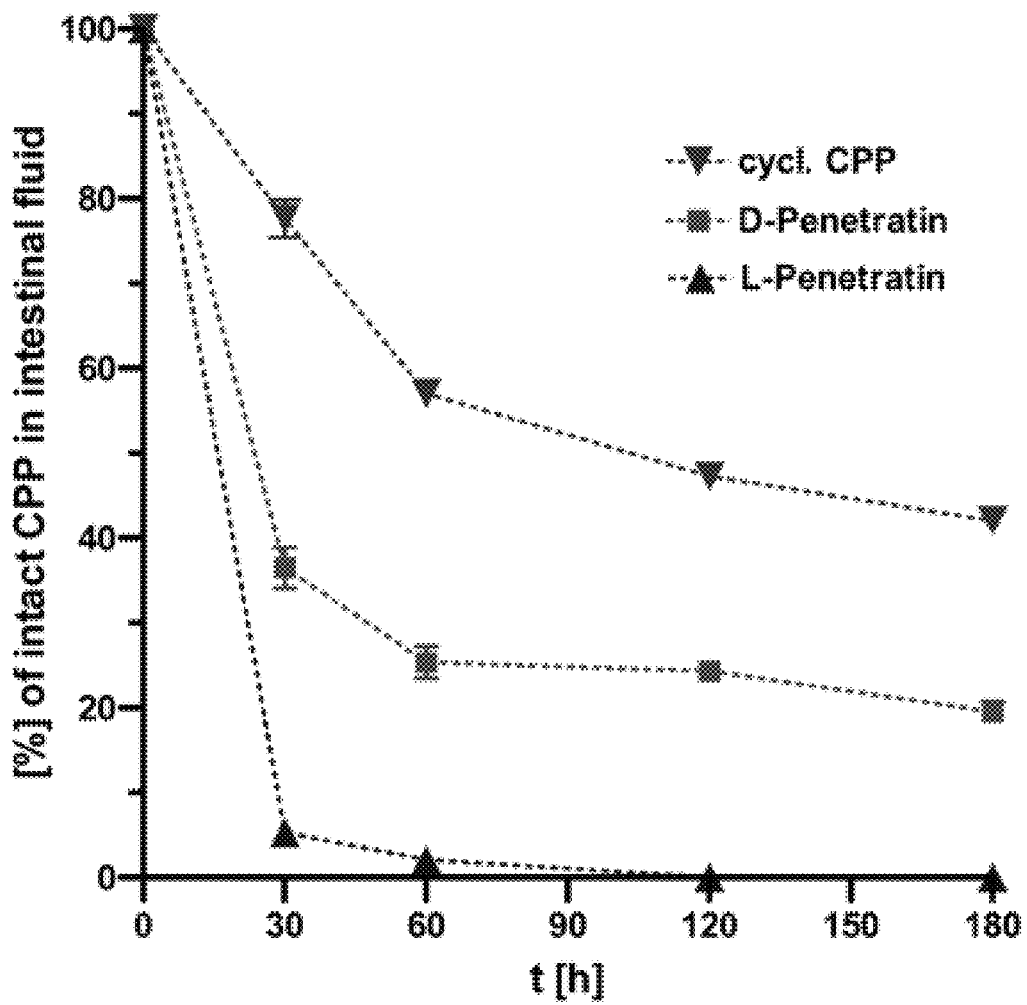

FIG. 13:
Recovery of intact CPPs in simulated intestinal fluid as detected by HPLC/MS at several time points.

Figure 14:
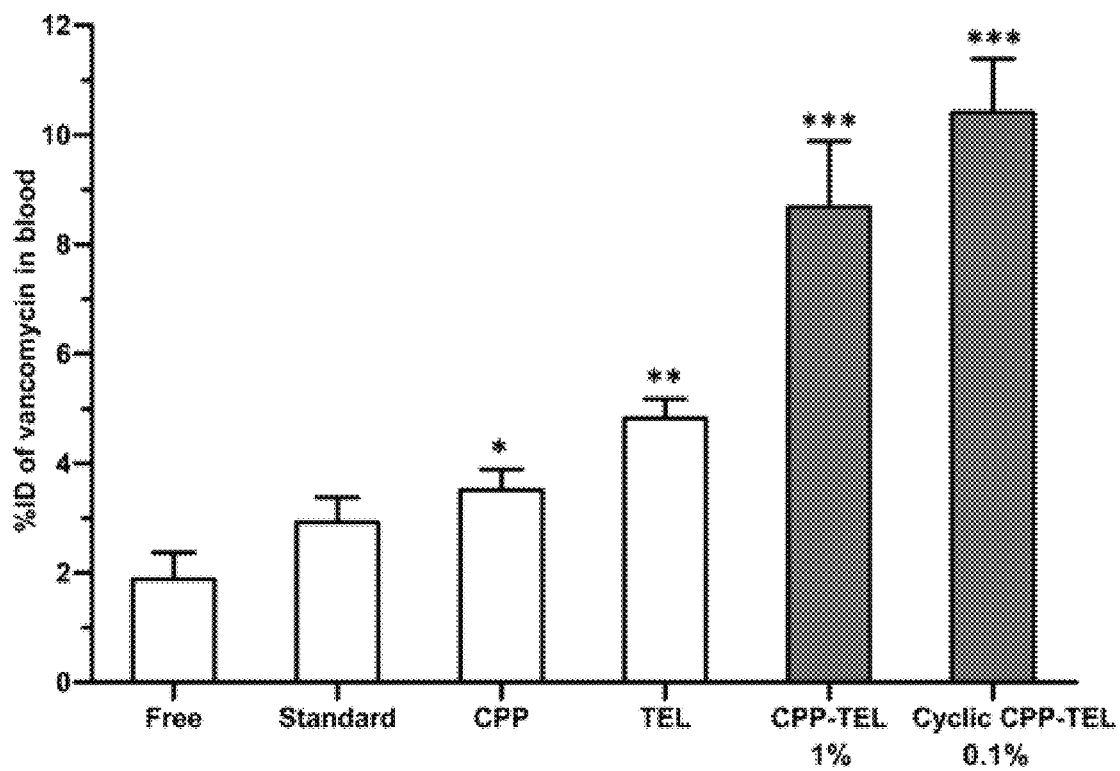
Figure 14:
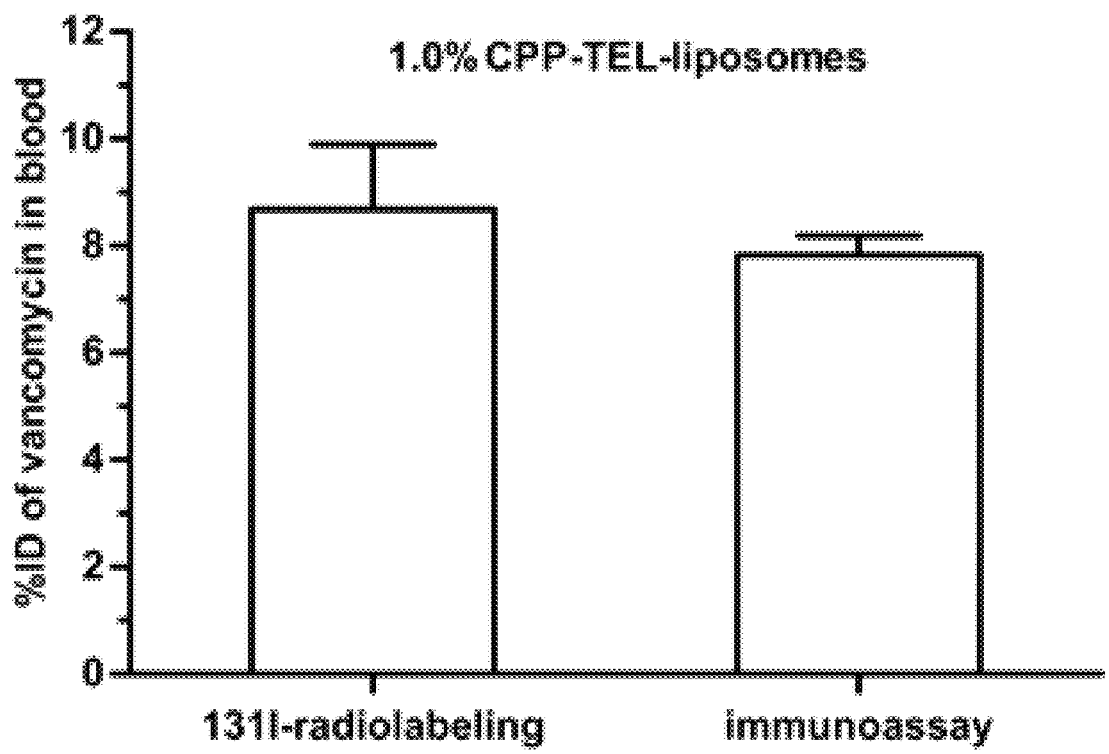

FIG. 14:
Several liposomal formulations were tested with either radiolabeled Vancomycin or by immunoassay and the blood levels of Vancomycin were determined at several time points.

Figure 15:
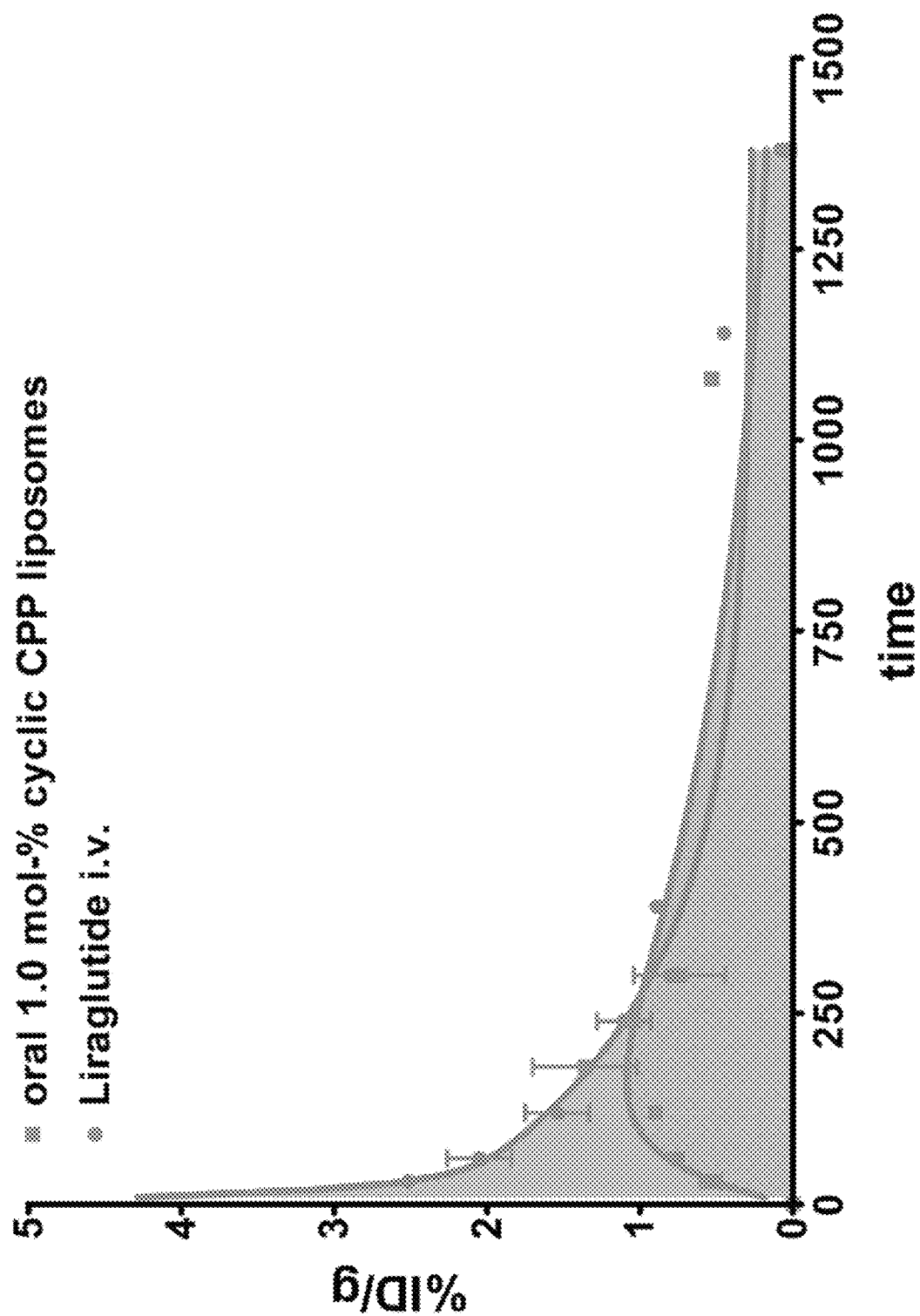

FIG. 15:
Bioavailability of oral Liraglutide (1 mol-% cyclic CPP-conjugate) in comparison with i.v. application.

Figure 16:
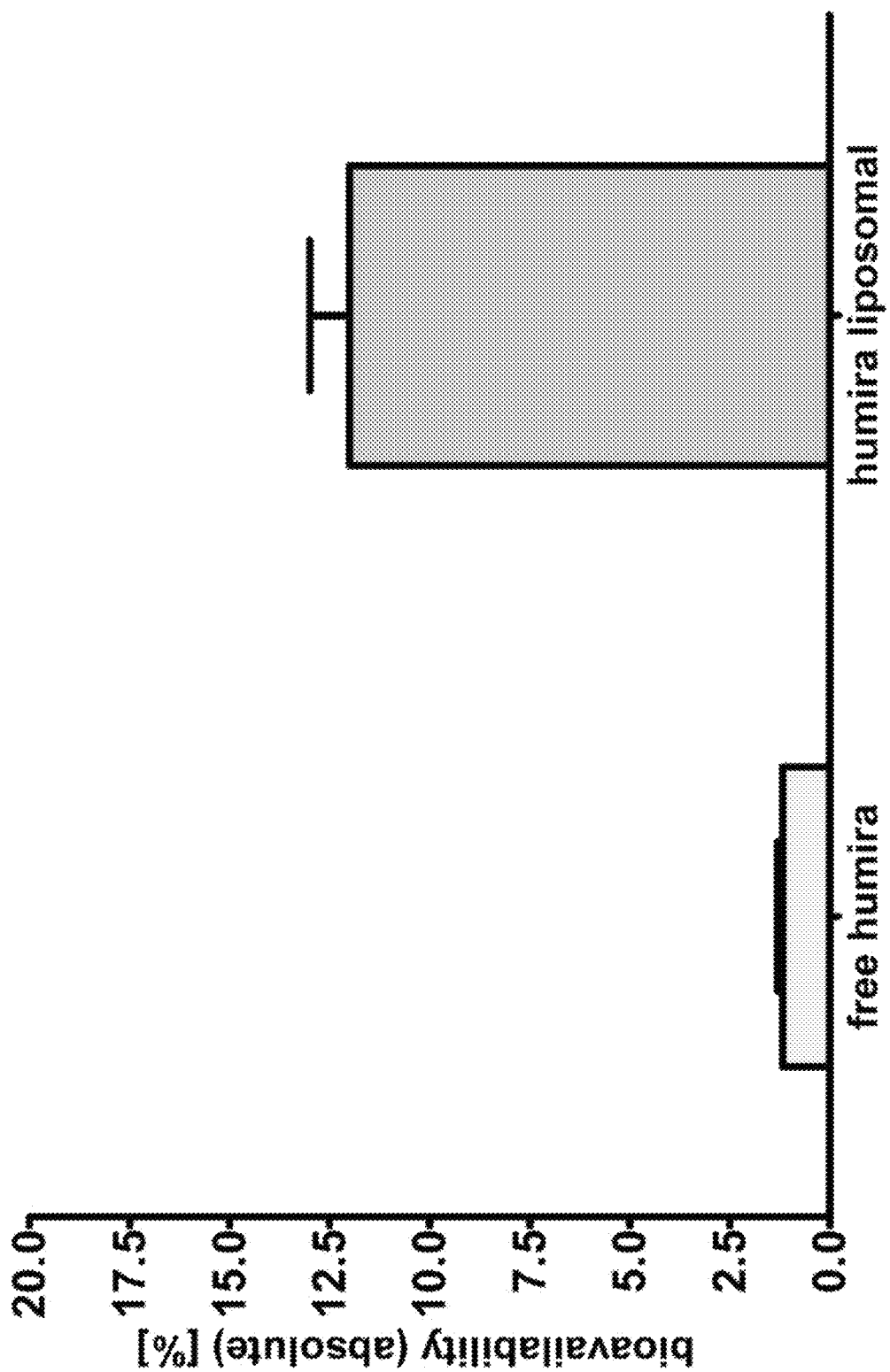

FIG. 16:
Bioavailability of the antibody Adalimumab (Humira®) in male Wistar rats.

Figure 17:
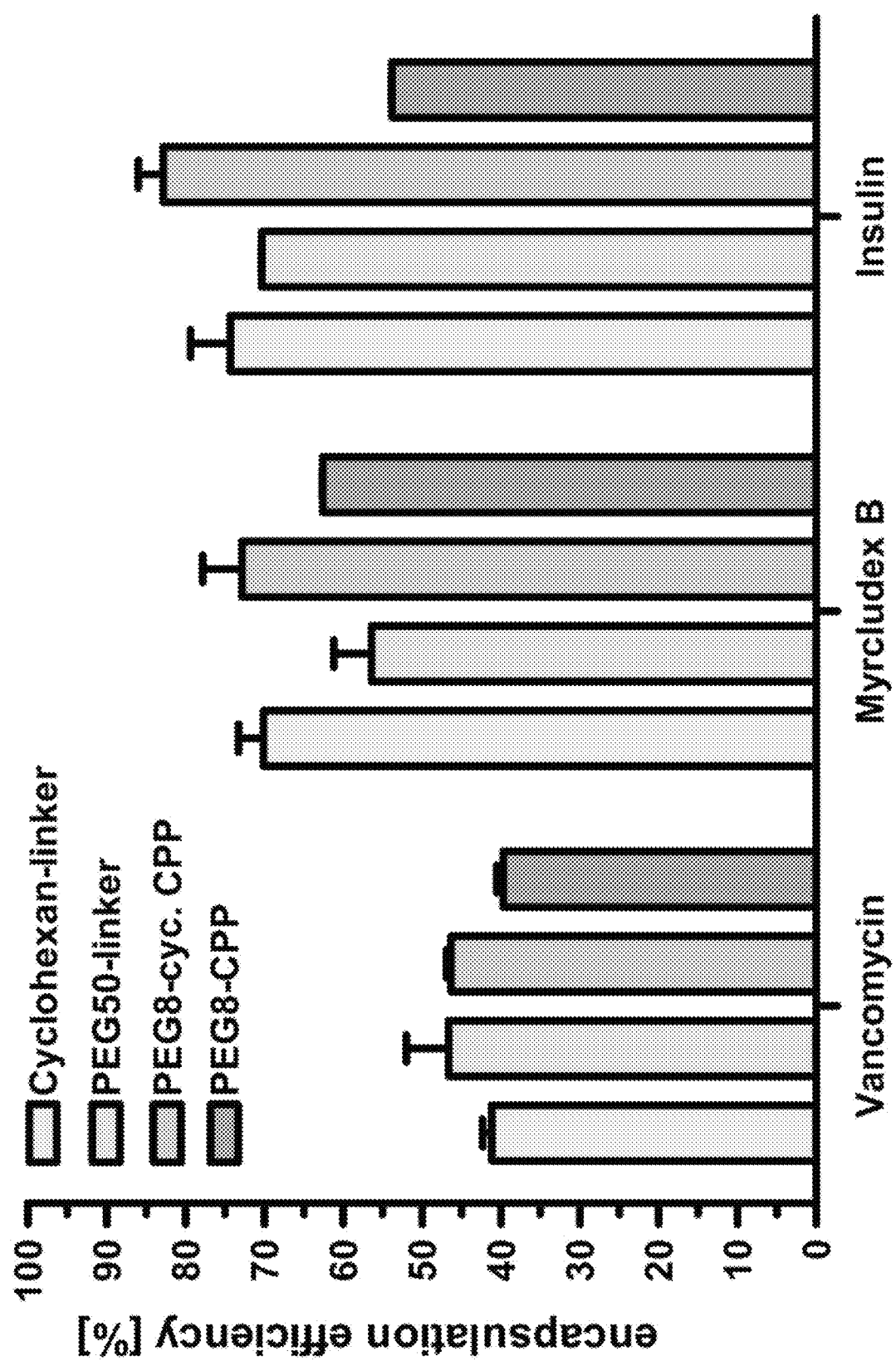

FIG. 17:
Determination of the incorporation efficiency of three peptide drugs using various PEG-linkers (different amounts of PEG-units).

Figure 18:
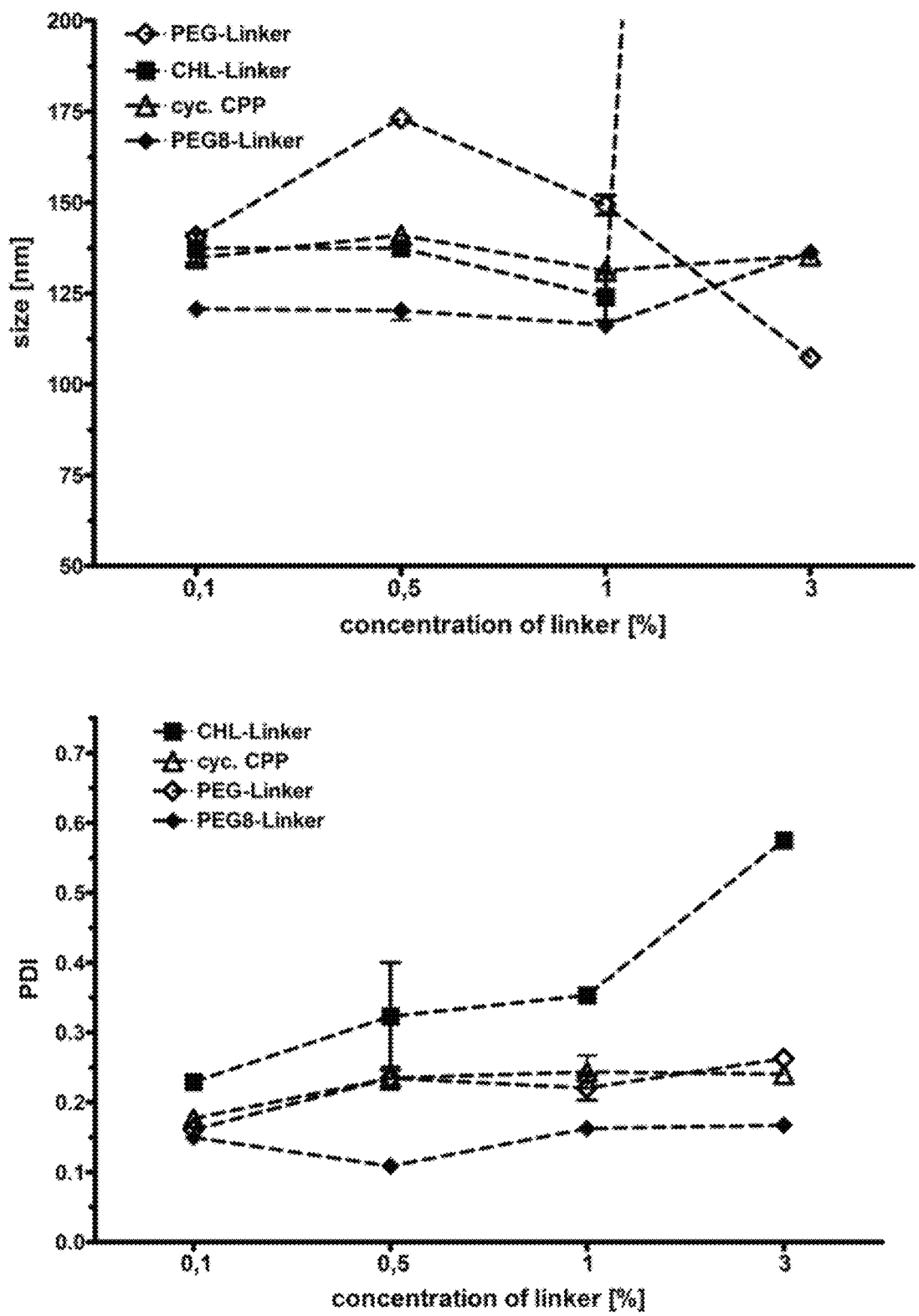

FIG. 18:
Size/PDI of liposomal formulations containing various concentrations of linkers which differ in the amount of PEG-units.

Figure 19:
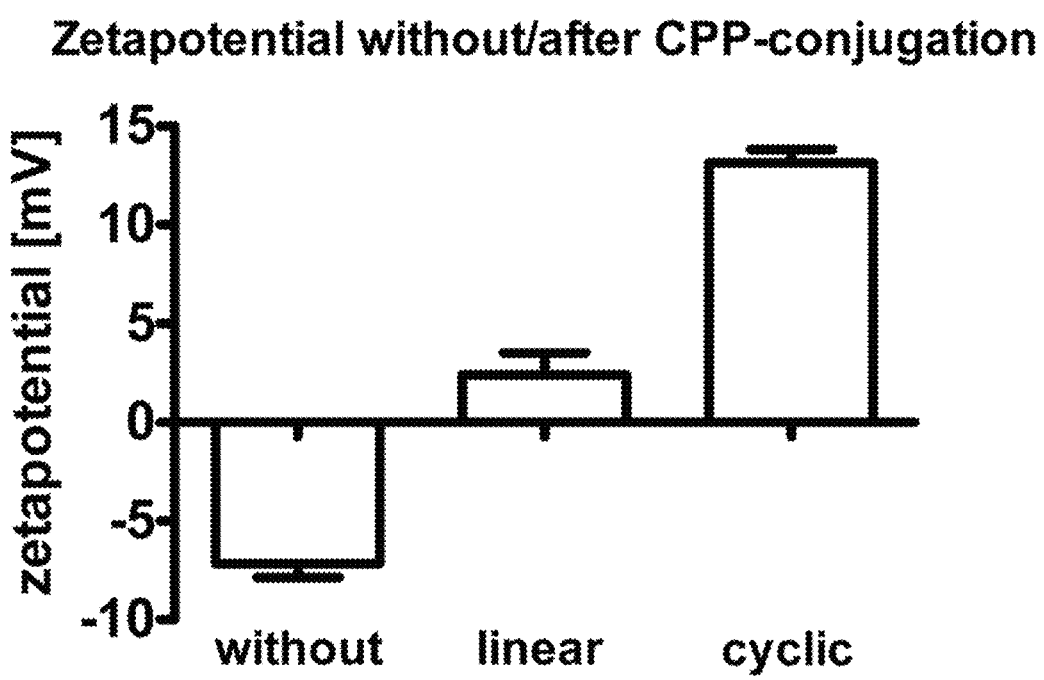

FIG. 19:
Zeta potential of liposomes with CPP-phospholipid-conjugates (1 mol-%) in comparison with standard liposomes.

Figure 20:
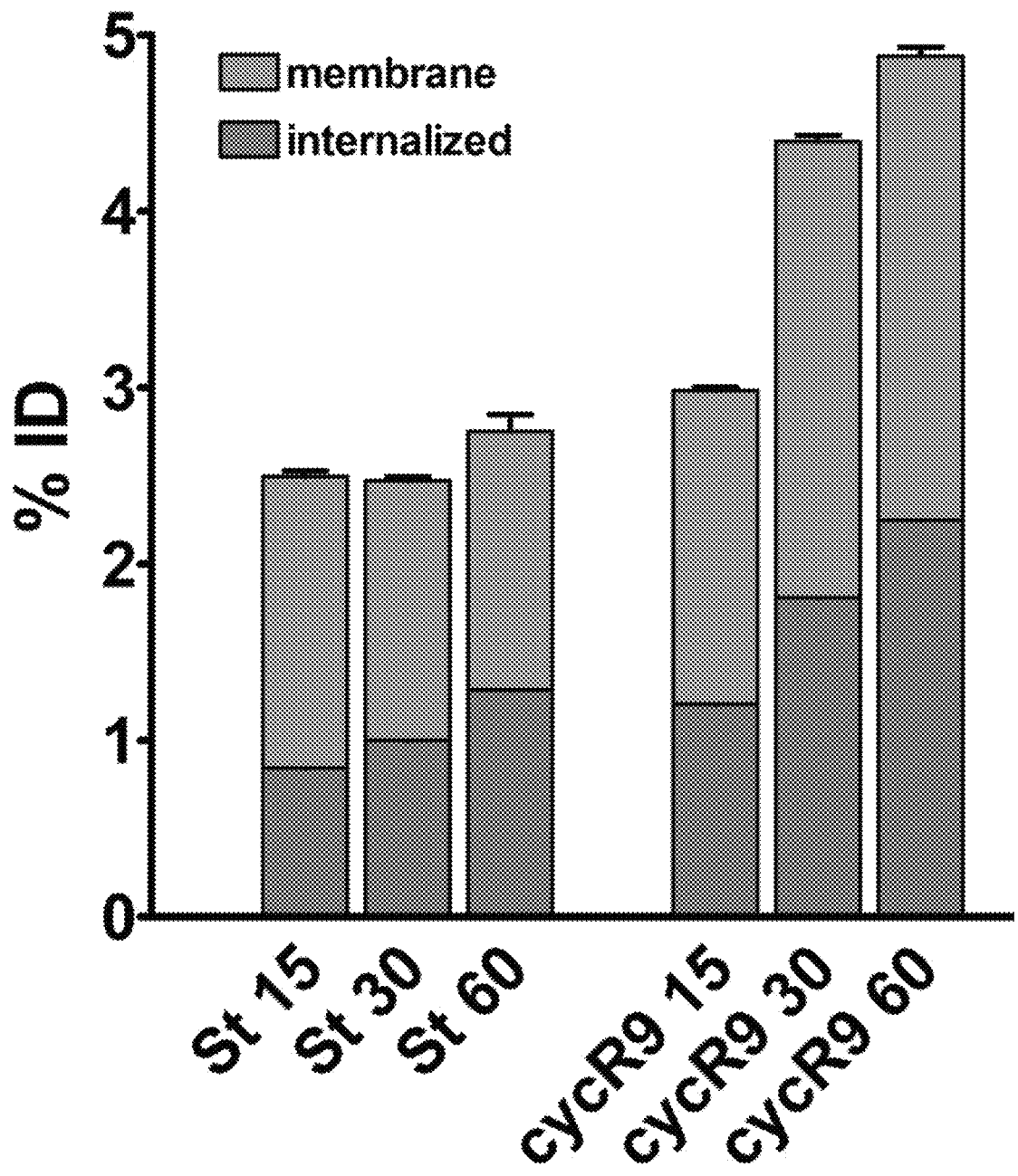

FIG. 20:
Cell binding assay of liposomes containing 1 mol-% of the cyclic CPP-phospholipid-conjugates in comparison with standard liposomes.

Figure 21:
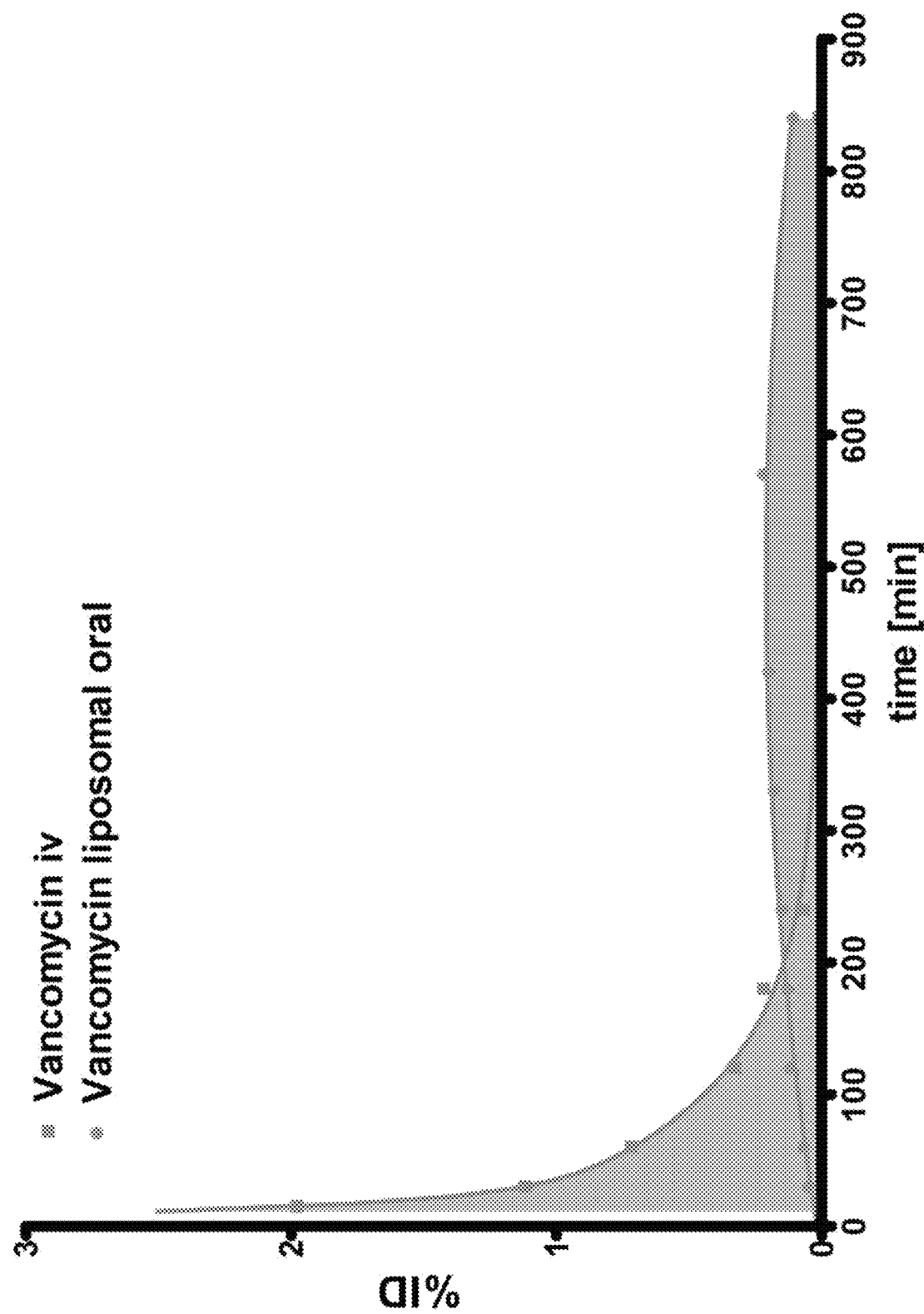

FIG. 21:
Bioavailability of oral Vancomycin (1 mol-% cyclic CPP-conjugate) in comparison with i.v. application.

Figure 22:
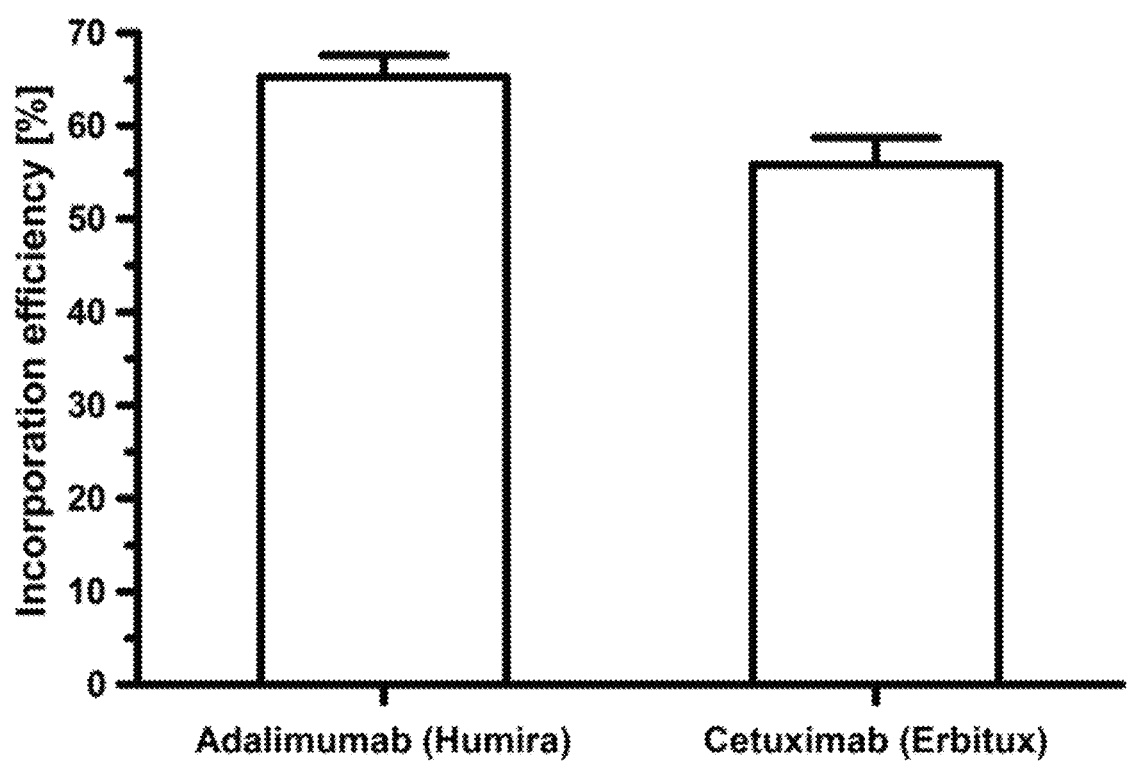

FIG. 22:
Incorporation efficiency of the two antibodies Adalimumab and Cetuximab.

Figure 23:
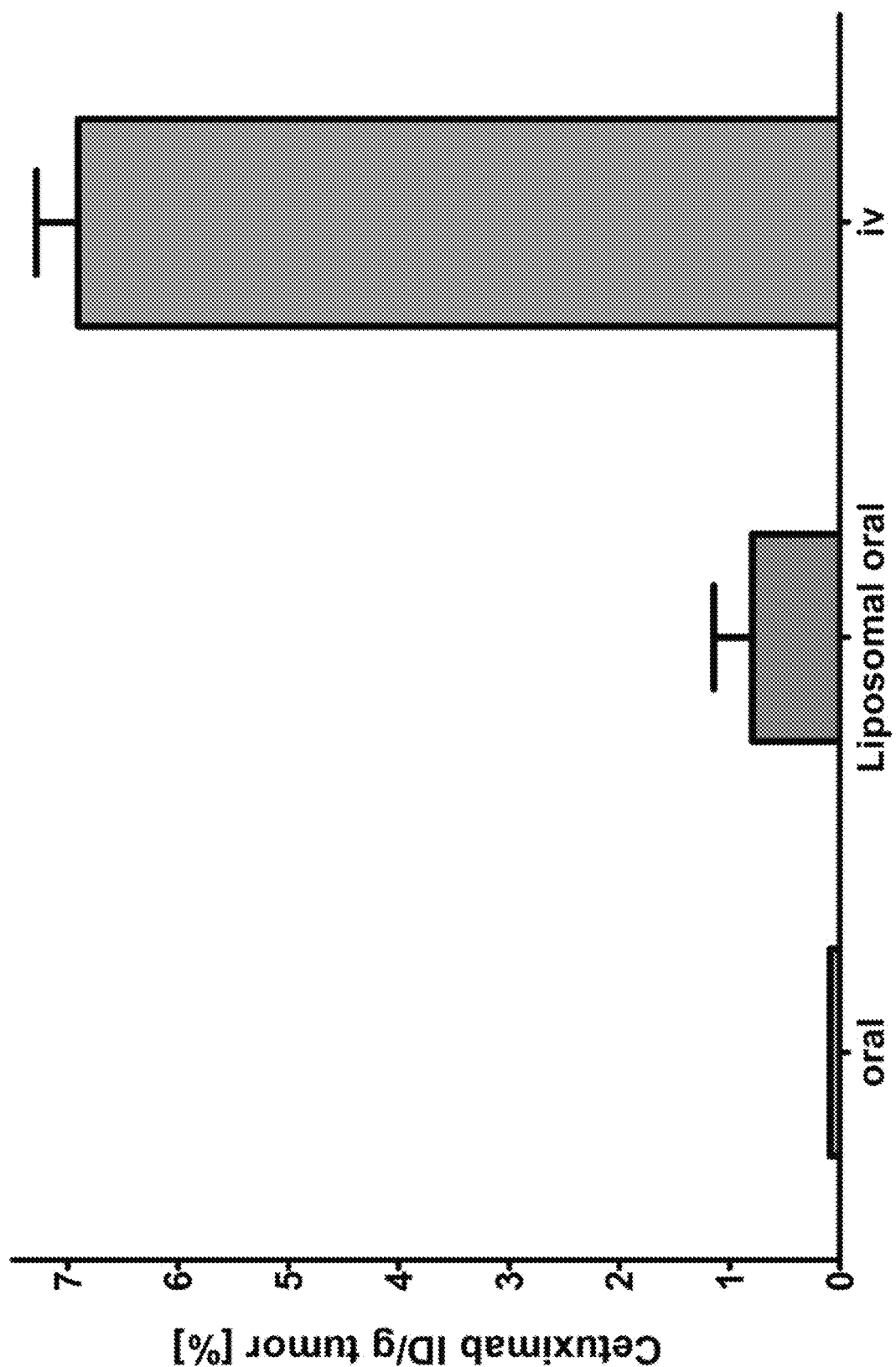

FIG. 23:
Tumor accumulation of the antibody Cetuximab in Balb/c mice.

Figure 24:
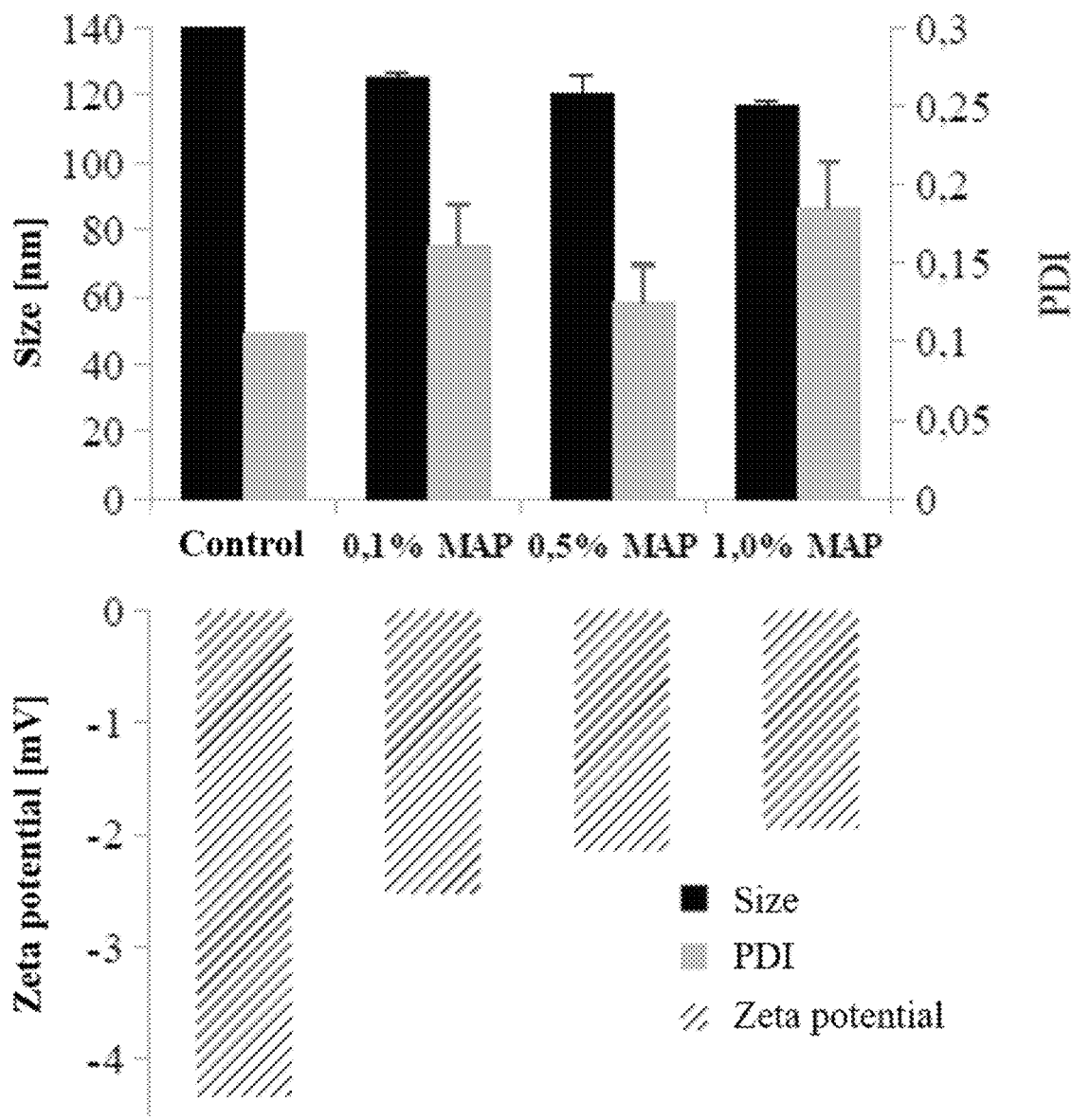

FIG. 24:
Particle characterization after incorporation of the MAP-phospholipid-conjugate into the liposomes.

The present invention will be further illustrated by the following examples without being limited thereto.

EXAMPLES

Material and Methods
Materials
Lecithin from Egg Bio Chemica (AppliChem GmbH, Darmstadt, Germany); cholesterol (Sigma Aldrich, Taufkirchen, Germany); 1,2-Dipalmitoyl-sn-Glycero-3-Phosphothioethanol (thiol-modified lecithin; Avanti® polar lipids, Alabama, USA); tetraether lipids (TELs) were isolated of S. acidocaldarius as described hereinafter; Dulbecco's phosphate buffered saline (Gibco® by life Technologies™, UK); glass beads (0.75-1.0 mm; Carl Roth GmbH+ Co. KG, Karlsruhe); NAP™-5 column (GE Healthcare, Buckinghamshire, UK); Triton™ X-100 (Sigma Aldrich, Taufkirchen, Germany); chloroform (Sigma Aldrich, Taufkirchen, Germany); methanol (Sigma Aldrich, Taufkirchen, Germany); Antra MUPS (Omeprazole, Astra Zeneca GmbH, Wedel); silica gel 60 (0.063-0.200 mm, Merck, Gernsheim, Germany); radioiodine (Perkin Elmer®, Boston, USA).

Isolation of TELs
Cell growth and lipid extraction were performed as known in the art. S. acidocaldarius was separated from the medium and lyophilized using a Delta 1-20 KD from Christ. The lipids were isolated by Soxhlet extraction with chloroform/methanol (2:1) as known in the art. The extracted solvent was removed by rotary evaporation (Rotavapor-R, Büchi Labortechnik AG, Flawil, Switzerland). Afterwards, the lipid mixture was dissolved in a mixture of chloroform, methanol and hydrochloric acid (8:3:1). The mixture was heated for 3 days to cleave the lipid head groups. Finally, the lipids were extracted with chloroform/methanol (2:1) from the water phase. Glycerylcaldityltetraether lipids (GCTE) were separated by silica gel column chromatography with water/methanol (1:1) as first eluent (for prewashing of the column), followed by water/methanol/chloroform (1:2.5:1) to remove unwanted lipids and methanol/chloroform (1:1) to obtain the GCTE fraction.

Synthesis of the CPP (Penetratin)-Phospholipid-Conjugate
1. Synthesis of the CPP Penetratin
Penetratin was produced by solid-phase synthesis using the fluorenylmethoxycarbonyl/t-butyl (Fmoc/tBu) chemistry on an Applied Biosystems 433A peptide synthesizer. Coupling conditions residues are performed as described. Purification was performed on a LaPrep P110 (VWR International) HPLC system equipped with a Reprosil™ Gold 120 C-18 column (4 μm, 150×20 mm). Water and acetonitrile containing 0.1% TFA were used as eluents with a flow rate of 20 ml/min. Separating condition was a linear gradient of 60-90% acetonitrile in 15 min. As eluents, 0.1% trifluoroacetic acid (TFA) in water (eluent A) and 0.1% TFA in acetonitrile (eluent B) were used. The identity of the peptides synthesized was verified by HPLC-MS (mass spectrometry) analysis (Exactive, Thermo Fisher Scientific).

2. Synthesis of the CPP (Penetratin)-Phospholipid-Conjugate

To 5 ml of a 1 mM solution of the thiol-modified phospholipid in a 2:1 mixture of DCM/DMSO, 20 mg of Penetratin-Cys predissolved in 200 μl DMSO were added. The reaction mixture was stirred overnight at room temperature. The solvents were evaporated and the crude product was dissolved in 20 ml of a 4:1 mixture of ACN/$H_2O$. Purification was performed on a LaPrep P110 (VWR International) HPLC system equipped with a Reprosil™ Gold 120 C-18 column (4 μm, 150×20 mm). Water and acetonitrile containing 0.1% TFA were used as eluents with a flow rate of 20 ml/min. Analytical analyses were performed on an Agilent 1100 HPLC system equipped with a Chromolithe® Performance RP-C18e column (100×4.6 mm). Water and acetonitrile containing 0.1% TFA were used as eluents with a flow rate of 2 ml/min. HPLC-MS analyses were done on an Agilent 1200 HPLC system equipped with a Waters® Hypersil Gold aq column (200×2.1 mm) followed by a Thermo Scientific Exactive mass spectrometer. Water and acetonitrile containing 0.05% TFA were used as eluents with a flow rate of 200 μl/min.

$^{131}$I-Radiolabeling of Vancomycin

For $^{131}$I-radiolabeling, a 1 mmol stock solution of the model substance vancomycin in PBS was prepared. The required amount of radioactive iodine-131 was added to 25 μl of the stock solution and the labeling was performed using the chloramine T method known in the art. The reaction mixture was purified by semi-preparative HPLC as known in the art. Afterwards, the purity of the radiolabeling was determined by radioHPLC (Agilent 1100 series) using a Chromolithe® Performance RP-C18 (100-3 mm) column applying a linear gradient of 0.1% TFA in water (eluent A) to 0.1% TFA in acetonitrile (eluent B) within 5 minutes; flow rate 2 ml/min; UV absorbance λ=214; γ-detection.

Liposome Preparation

Liposomes were prepared by the DAC-method using a SpeedMixer™ (DAC150FVZ Hauschild Engineering GmbH & Co. KG, Hamm, Germany). First of all, the lipids were dissolved in chloroform/methanol 9:1 to obtain 100 mmol stock solutions while the CPP was dissolved in chloroform/methanol 1:1 (1 mmol stock). The required amount of the CPP stock solution (0.1-1.0 mol-%) was added to the lipid mixture (85 mol-% EPC, 10 mol-% cholesterol and 5 mol-% TEL) and the organic solvent was evaporated by a nitrogen stream. Afterwards, the resulting lipid film was dried for 1 h in a vacuum chamber. Before starting the speed mixing process, 20 mg of 0.075-1.00 mm glass beads were added. The liposomes were prepared by speed mixing and the addition of different amounts of the incorporated substance (e.g. vancomycin—1 mmol stock, dissolved in PBS; run 1) or PBS (run 2/3) in 3 runs to a total volume of 250 μl (cf. Table 1). For comparison, standard liposomes (85 mol-% EPC; 15 mol-% cholesterol) were prepared in the same way.

TABLE 1

Speed mixing process performed in 3 runs

| | Time [min] | Volume calculation | Volume [μl] |
|---|---|---|---|
| Run 1 | 30 | Overall lipid mass [mg] * 1.5 | 28.5 |
| Run 2 | 5 | Overall lipid mass [mg] + 1. volume | 47.5 |
| Run 3 | 1 | Total volume-1. Volume-2 * 2. volume | 126.5 |

Encapsulation Efficiency

The encapsulation efficiency of vancomycin was determined by reversed phase (rp) HPLC (Agilent 1100 Series) using a C18 column (Chromolithe® Performance RP-18e, 100-3 mm) applying a linear gradient of 0.1% TFA in water (eluent A) to 0.1% TFA in acetonitrile (eluent B) within 5 minutes; flow rate 2 ml/min; UV absorbance λ=214 nm. After the speed mixing process, the liposomes were divided in two parts with 100 μl each. Part 1 was used to calculate the 100% value by destroying the liposomes by the addition of 50 μl 10% Triton™ X-100 and determining the AUC of vancomycin by rpHPLC. Part 2 was purified by Sephadex G-25 gel filtration chromatography (NAP™-5 column) and afterwards handled in the same way as part 1. The encapsulation efficiency E (%) was determined by the following equation after the correction of the dilution of part 2:

$$E(\%) = \frac{[AUC] \text{vancomycin part 2}}{[AUC] \text{vancomycin part 1}} * 100\%$$

Whereby [AUC] vancomycin part 2 is the purified liposomal fraction and [AUC] vancomycin part 1 is the 100% value after the liposomal preparation.

Particle Characterization

1. Particle size, Polydispersity index (PDI) and Zeta Potential

The particle size, PDI and zeta potential of all liposomal formulations were determined at room temperature using a Zetasizer Nano ZS from Malvern™ (Malvern Instruments Ltd., Worcestershire, United Kingdom). Size and PDI were measured after the dilution to a concentration of 0.076 mg/ml with PBS while the zeta potential was determined after the dilution to a concentration of 0.95 mg/ml by a 50 mmol phosphate buffer. The measurements were conducted by using the automatic mode and the average of three measurements. The size is specified in nm and the zeta potential in mV, while the PDI is a dimensionless value.

2. Kryo-Electron Micrographs (EM)

As known in the art, in order to determine the size and lamellar structure of the CPP-TEL-Liposomes, samples were frozen using a FEI Vitrobot on 2/2 Quantifoil grids. Afterwards, each sample was glow discharged for 3 s and blotted at 4° C. and 100% humidity for 8-10 s. The grids were observed in a Krios microscope operated at 200 kV and liquid nitrogen temperature. The pictures of the CPP-liposomal samples were taken at 64 000× magnification.

Long Term Storage Stability

1. Freeze Drying Using Sucrose as Lyoprotector at Different Molar Ratios

All liposomal formulations were freeze dried in a Delta 1-20 KD from Christ. The main drying was carried out at −20° C. for two days with a following secondary drying at 0° C. for at least six hours. Sucrose was used as lyoprotector in a range of 100-500 nm since it has been found to be a good lyoprotector before. Briefly, the liposomes were prepared as described above with the difference that during the 3 runs instead of the PBS-buffer the desired concentration of sucrose in PBD was added. The liposomal suspension was partitioned into 50 µl per Eppendorf vessel and freeze-dried. The freeze-fried liposomes were rehydrated with 50 µl PBS and the size and PDI were determined using the Zetasizer Nano ZS from Malvern™ as described above.

2. Residual Moisture of Lyophilisates

The residual moisture of CPP-TEL-liposomes was determined by a moisture meter (Kern & Sohn, Balingen, Germany) using 100 mg of the freeze dried liposomes by heating up to 120° C. in 90 seconds.

Proof of Concept: Animal Studies

1. Blood Levels of $^{131}$I-Labeled Vancomycin of Different Formulations

The animal study was performed according to local authorities using male Wistar rats with a body weight of about 220-250 g. In order to determine the blood levels of different formulations, vancomycin was radiolabeled by $^{131}$I and incorporated into several liposomal formulations. Blood levels of vancomycin 1 h after oral administration were measured by direct counting of the radioactivity using a Berthold LB 951 G counter in comparison with standards. Briefly, five groups (n=6) of Wistar rats were formed. The day before the experiment, the rats were pretreated with suspended Antra MUPS™ (omeprazole) by gavage (10 mg per rat) because recent studies showed that pretreatment with the proton pump inhibitor omeprazole decreases the diffusion of protons into liposomes and, as a consequence, decreases the denaturation of the encapsulated agents by raising the pH in the stomach. The rats were kept without food 12 h before the experiment but with free access to water. Oral application took place by gavage. The rats were sacrificed after 1 h, the blood samples were taken, weighed and the radioactivity in the blood samples was measured using a Berthold LB 951 G counter in comparison with standards. The blood-associated activity was related to the totally injected dose (ID) and expressed as a percentage of the totally injected dose per gram tissue (% ID). Afterwards, the total blood level (% ID) was calculated.

2. Determination of Vancomycin Blood Levels by Immunoassay

In order to verify the values obtained by the measurement of radioactive blood samples, a vancomycin immunoassay (ADVIA Centaur® VANC ReadyPack®, Siemens, Tarrytown, USA) of the CPP-TEL-vancomycin-liposomal formulation was performed. Similar to the radiolabeling study, 500 µl of the CPP-TEL-vancomycin-liposomes were administered to 250 g male Wistar rats (n=6) by gavage. The day before the experiment, the rats were pretreated with suspended Antra MUPS™ (omeprazole) by gavage (10 mg per rat). 1 h after the oral administration, the rats were sacrificed, blood samples were taken, plasma was separated and the amount of vancomycin was determined by the immunoassay described above.

Example 1

Isolation of TELs

The isolation procedure yielded tetraether lipids in purified form with only slight variations in the number of pentyl rings (3 to 5) in the lipophilic chains as determined by mass spectrometry and thin layer chromatography. The number of rings is influenced by the temperature during cultivation of the archaea. On average 1 g of tetraether lipids could be obtained per 400 g of wet cell mass.

Example 2

Synthesis and Characterization of the CPP-Phospholipid-Conjugate

The CPP (Penetratin)-phospholipid-conjugate could be obtained in high purity as determined by mass spectrometry (FIG. 5). The total yield of the product was about 59% after purification by preparative HPLC.

Example 3

$^{131}$I-Radiolabeling of Vancomycin

The $^{131}$I radiolabeling of Vancomycin yielded the desired product in high purity (>95%) as determined by radioHPLC (FIG. 6). The labeling efficiency using the chloramine T method was about 60% of the radioactivity applied.

Example 4

Encapsulation Efficiency

The CPP-TEL-vancomycin-liposomes showed an encapsulation efficiency of 35.38±1.65% which is comparable with the determined value of the standard liposomes (38.73±1.23%).

Example 5

Particle Characterization

1. Particle Size, Polydispersity Index (PDI) and Zeta Potential

The applied DAC-method yielded CPP-TEL-vancomycin-liposomes with high homogeneity in size, PDI and incorporation efficiency (cf. Table 2). Compared with the standard liposomes, size and PDI showed a slightly increase, while the CPP-TEL-vancomycin-liposomes are characterized by a more positive zeta potential than the standard liposomes.

TABLE 2

Particle characterization of CPP-TEL and standard liposomes

| Liposomal formulation | Size [nm] | PDI | Zeta potential [mV] |
|---|---|---|---|
| CPP-TEL-vancomycin | 151.3 ± 1.9 | 0.257 ± 0.035 | 0.068 ± 0.032 |
| Standard vancomycin | 127.7 ± 1.5 | 0.163 ± 0.02 | −5.46 ± 0.184 |

2. Kryo-Electron Micrographs (EM)

The Kryo-electron micrograph (FIG. 7) shows the size and lamellar structure of CPP-TEL-vancomycin-liposomes containing 85 mol-% lecithin; 10 mol-% cholesterol; 5 mol-% TEL and 0.1 mol-% penetratin. Most of the pictured liposomes show mono-respectively up to three lamellar layers.

Example 6

Long Term Storage Stability

1. Freeze Drying Using Sucrose as Lyoprotector at Different Molar Ratios

The freeze drying of the CPP-TEL-liposomes containing sucrose in different molar ratios as lyoprotector resulted in a comparable size and PDI for certain molar ratios compared with the data measured before the freeze drying process (FIG. 8 A, B). Regarding this liposomal formulation, the lowest limit of sucrose is 300 mmol but best results were obtained by the use of a 500 mM concentration of sucrose. A further increase in the lyoprotector's concentration (more than 500 mmol sucrose) does not provide better results regarding size and PDI of the liposomes.

2. Residual Moisture after the Freeze Drying Process

Due to the very poor stability of liposomal suspensions, it would be desirable to obtain lyophilisates which show very low residual moisture in order to ensure the long term stability of the lyophilized liposomes. The residual moisture of the CPP-TEL liposomal formulation containing 500 mmol sucrose as lyoprotector was 2.88%±0.79%.

Example 7

Proof of Concept: Animal Studies

1. Blood Levels of $^{131}$I-Labeled Vancomycin of Different Formulations

The proof of concept study showed a 3-fold increase of vancomycin blood levels for the CPP-TEL-liposomes compared with the standard liposomes. The addition of only one additional component (either CPPs or TELs) showed only a slight increase in the vancomycin blood levels. This emphasizes the necessity of both components in one liposomal composition to provide a tool for the oral delivery of macromolecules (FIG. 9).

2. Determination of Vancomycin Blood Levels by Immunoassay

The determination of vancomycin blood levels by immunoassay showed comparable results as the radiolabeling study (7.83% vs. 8.68%) (FIG. 10).

Example 8

In the present invention a novel class of CPP-phospholipid-conjugates was established. Two different variants of CPPs were used (FIG. 11), on the one side linear CPPs (model CPP Penetratin, d/l-form) and on the other side cyclic CPPs (a cyclic R9 derivative). Cyclic CPPs were used due to higher enzymatic stability in intestinal fluid as detected by mass spectrometry (FIG. 13). Furthermore, it could be shown that the linear CPP Penetratin is more stable if it is constituted of D-amino acids.

FIG. 12 shows the four model substances Vancomycin, Insulin, Liraglutide and the antibody Adalimumab (Humira®). These substances cover the whole range of molecular weight of macromolecular drugs and demonstrate that the novel liposomal formulations of the present invention can serve as platform for macromolecular drugs in general.

Method for the Stability Assays of CPPs in Intestinal Fluid—Stability of CPPs in Simulated Intestinal Fluid.

All CPPs (1 mg/ml in water) were diluted 1:1 (v/v) with simulated intestinal fluid and incubated at 37° C. under constant shaking as known in the art. After 0, 15, 30 and 60 min the samples were analyzed by HPLC/MS in order to detect the recovery of intact CPP and were compared in relation with the initial solution.

Example 9

A variety of liposomal formulations was tested with the model substance Vancomycin in male Wistar rats (200-250 g). The measurement of the radiolabeled blood levels of Vancomycin showed a significant increase in the oral availability of Vancomycin using a liposomal formulation containing 1 mol-% of the linear CPP-phospholipid conjugate. Nevertheless, another formulation containing only 0.1 mol-% of the cyclic CPP-phospholipid-conjugates showed a higher increase in Vancomycin blood levels accompanied by the benefit, that minor amounts if the conjugates are required. The results obtained were checked by immunoassay of Vancomycin and similar blood levels could be measured (FIG. 14).

Method for the Animal Trials Using the Glycopeptide Drug Vancomycin as Model Substance The animal study was performed according to local authorities using male Wistar rats with a body weight of about 200-250 g. In the proof of concept study, Vancomycin was radiolabeled with $^{131}$I and incorporated into various liposomal formulations as described previously. 1 h after oral administration, the blood levels of Vancomycin were measured by direct counting of the radiolabeled sample. Briefly, groups (n≥3) of male Wistar rats were formed. Prior to 12 h of the experiment, the rats were kept without food, but with free access to water. Oral application of the liposomes and the free peptide took place by gavage. The blood was removed, weighed and the radioactivity was measured using a Berthold LB 951 G counter in comparison with standards. The blood-associated activity was related to the total injected dose (ID) and expressed as a percentage of the total injected dose per gram of tissue (% ID/g). The statistical data were processed using the Prism® software (GraphPad Software, San Diego, Calif., USA) and presented as mean±standard deviation of the mean (S.D.). The different groups of the animal trial were compared by one-way ANOVA test using the Prism® software and considered significant at *p<0.05, p<0.01 and *p<0.001 (FIG. 14).

Example 10

In one further study, the bioavailability of the peptide drug Liraglutide was examined. For this reason, the drug was injected i.v. and the blood levels were compared with the oral liposomal formulation containing 1 mol-% of the cyclic CPP-liposomes. Regarding this peptide drug, the bioavailability by the use of our liposomal formulation is >50% in comparison with the i.v. application of Liraglutide (FIG. 15).

Method for the Animal Trials Using Liraglutide as Model Substance for the Determination of the Bioavailability.

The animal study was performed according to local authorities using male Wistar rats with a body weight of about 200-250 g. For the determination of the bioavailability the anti-diabetic drug Liraglutide was radiolabeled with $^{131}$I and incorporated into the liposomal formulation containing 1 mol-% of the cyclic CPP-phospholipid-conjugate and compared with Liraglutide i.v. as described previously. At several time points, the blood levels of Liraglutide were measured by direct counting of the radiolabeled sample. Briefly, groups (n≥3) of male Wistar rats were formed. Prior to 12 h of the experiment, the rats were kept without food, but with free access to water. Oral application of the liposomes took place by gavage. The blood was removed, weighed and the radioactivity was measured using a Berthold LB 951 G counter in comparison with standards. The blood-associated activity was related to the total injected dose (ID) and expressed as a percentage of the total injected dose per gram of tissue (% ID/g). The statistical data were processed using the Prism® software (GraphPad Software, San Diego, Calif., USA) and presented as mean±standard deviation of the mean (S.D.) (FIG. 15).

Example 11

In one further pilot trial, the oral availability of Adalimumab (Humira®) was examined. For this reason, the antibody was radiolabeled with $^{131}$I, incorporated into the liposomes containing 1 mol-% of the cyclic CPP-conjugate, orally administered and compared with the radiolabeled free peptide. The incorporation efficiency of the antibody into the liposomes was about 60% as detected by direct measurements of the radiolabeled antibody before and after purification. Again, a strong increase in the oral availability of Adalimumab could be detected (FIG. 16). Therefore it could be claimed, that this novel liposomal formulation is also suitable for macromolecular drugs with a molecular weight >100 kDa such as antibodies.

Method for the Animal Trials Using the Antibody Adalimumab (Humira®) as Model Substance for the Determination of the Bioavailability (Absolute).

The animal study was performed according to local authorities using male Wistar rats with a body weight of about 200-250 g. For the determination of the bioavailability (absolute), the antibody Adalimumab (Humira®) was radiolabeled with $^{131}$I and incorporated into the liposomal formulation containing 1 mol-% of the cyclic CPP-phospholipid-conjugate and compared with the free antibody as described previously. After 6 h, the blood levels were measured by direct counting of the radiolabeled sample. Prior to 12 h of the experiment, the rats were kept without food, but with free access to water. Oral application of the liposomes and the radiolabeled free antibody took place by gavage. The blood was removed, weighed and the radioactivity was measured using a Berthold LB 951 G counter in comparison with standards. The blood-associated activity was related to the total injected dose (ID) and expressed as a percentage of the total injected dose per gram of tissue (% ID/g) (FIG. 16).

Example 12

In another study, the influence of the linker used for coupling of the CPPs to the head group-modified phospholipid was examined and it could be shown, that the incorporation efficiency of peptide drugs depends on the amount of PEG units of the linker (FIG. 17). In FIG. 18, several amounts (0-3 mol-%) of CPP-phospholipid conjugates using various linkers were incorporated into the liposomes and afterwards liposomal size and PDI were determined. It could be shown that PEG-linkers show the best results, wherein PEG-linkers consisting of 8-50 individual PEG units are preferred.

Method for the Examination of Different PEG-Linkers.

The encapsulation efficiency of the peptide drugs was determined by reversed phase HPLC (Agilent 1100 Series) using a C18 column (Chromolith® Performance RP-18e, 100-3 mm) applying a linear gradient of 0.1% TFA in water (eluent A) to 0.1% TFA in acetonitrile (eluent B) within 5 minutes (flow rate 2 ml/min; UV absorbance $\lambda$=214 nm). After the speed mixing process, the liposomes were divided in two parts with 100 µl each. Part 1 was used to calculate the 100% value obtained by destroying the liposomes by the addition of 50 µl 1% Triton™ X-100 and determining the area under the curve (AUC) of the peptide drug by HPLC. Part 2 was purified by Sephadex G-25 gel filtration chromatography (NAP™-5 columns) and quantified as part 1. In order to determine the potential loss of lipids on the NAP™-5 columns during the purification of part 2, the concentration of cholesterol in the liposomal suspension was measured directly after the speed mixing process and after the purification using NAP™-5 columns. For both measurements, the liposomes were dissolved 1:10 (v/v) in methanol. Cholesterol was quantified by HPLC applying an isocratic gradient of acetonitrile/methanol (80:20 v/v) within 15 minutes (flow rate 2 ml/min; UV absorbance $\lambda$=208 nm) on a RP-18 column. The concentration of cholesterol before and after the purification step was compared and the correction factor C was determined in order to include the loss of lipids on the NAP™-5 columns into the calculation of the encapsulation efficiency. The encapsulation efficiency E (%) was calculated using the following equation:

$$E(\%) = ([AUC] \text{ peptide drug part 2})/([AUC] \text{ peptide drug part 1}) \times 100\% \times C$$

Whereby [AUC] peptide drug 2 is the concentration of the peptide drug in the purified liposomal fraction and [AUC] peptide drug part 1 is the concentration of the peptide drug in the liposomal suspension. C is the correction factor considering the loss of lipids on the NAP™-5 columns.

Example 13

After purification of the liposomal suspension by size exclusion chromatography, the zeta potential of the CPP-modified liposomes showed a strong increase compared with the unmodified liposomes due to the positive charged amino acids of the CPPs (FIG. 19) confirming the successful incorporation of the conjugates into the liposomes.

Methods for Zeta Potential Measurement.

The zeta potential of the liposomes was determined at room temperature using the automatic mode of a Zetasizer Nano ZS from Malvern™ (Malvern Instruments Ltd., Worcestershire, United Kingdom). The particle size, PDI and zeta potential of all liposomal formulations were determined at room temperature using a Zetasizer Nano ZS from Malvern™ (Malvern Instruments Ltd., Worcestershire, United Kingdom). Size and PDI were measured after dilution to a lipid concentration of 0.076 mg/ml with a 10 mM phosphate buffer with a pH of 7.4 using the automatic mode. The zeta potential was determined after dilution to a lipid concentration of 0.95 mg/ml by a 50 mM phosphate buffer with a pH of 7.4. The default settings of the automatic mode of the Zetasizer Nano ZS from Malvern™ (Malvern Instruments Ltd., Worcestershire, United Kingdom) were the following: number of measurements=3; run duration=10 s; number of runs=10; equilibration time=60 s; refractive index solvent 1.330; refractive index polystyrene cuvette 1.590; viscosity=0.8872 mPa s; temperature=25° C.; dielectric constant=78.5 F/m; backscattering mode (173°); automatic voltage selection; Smoluchowski equation, phosphate buffer pH 7.4.

Example 14

The binding capacity of liposomes containing the cyclic CPP-phospholipid-conjugates in comparison with standard liposomes was tested by radiolabeling of the antibody matuzumab. The liposomes containing the novel conjugate showed a significant higher binding capacity than the standard liposomes (FIG. 20).

Methods for Binding Assay.

Caco-2 cells were seeded in 6 well plates. After differentiation for 2 weeks, 1 ml of a liposomal sample was added after removal of the growth medium. The cells were washed with phosphate buffer after incubation at 37° C. for 15, 30 and 60 minutes. Afterwards, the cells were incubated for 5 min with 1 ml of 1 mol glycine buffer pH 2.2. 0.3 mol NaOH was added and cell lysis took place by 0.25% SDS. The glycine buffer and the cell lysis fraction were collected and the amount of radioactivity was measured using a Berthold LB 951 G counter in comparison with standards.

Example 15

In one further study, the bioavailability (absolute) of the peptide drug Vancomycin was examined. For this reason, the drug was injected i.v. and the blood levels were compared with the oral liposomal formulation containing 1 mol-% of the cyclic CPP-liposomes. Regarding this peptide drug, the bioavailability by the use of our liposomal formulation is up to 50% in comparison with the i.v. application of Vancomycin (FIG. 21).

Method for the Animal Trials Using Vancomycin as Model Substance for the Determination of the Bioavailability (Absolute).

The animal study was performed according to local authorities using male Wistar rats with a body weight of about 200-250 g. For the determination of the bioavailability (absolute) the glycopeptide antibiotic Vancomycin was radiolabeled with $^{131}$I and incorporated into the liposomal formulation containing 1 mol-% of the cyclic CPP-phospholipid-conjugate and compared with Vancomycin i.v. as described previously. At several time points, the blood levels of Vancomycin were measured by direct counting of the radiolabeled sample. Briefly, groups (n≥3) of male Wistar rats were formed. Prior to 12 h of the experiment, the rats were kept without food, but with free access to water. Oral application of the liposomes took place by gavage. The blood was removed, weighed and the radioactivity was measured using a Berthold LB 951 G counter in comparison with standards. The blood-associated activity was related to the total injected dose (ID) and expressed as a percentage of the total injected dose per gram of tissue (% ID/g).

Example 16

In another study, the incorporation efficiency of two antibodies, namely Adalimumab and Cetuximab were determined as described previously (FIG. 22). It could be shown that both antibodies also show high incorporation efficiencies comparable to peptide drugs (about 50-70%).

Example 17

In order to determine the tumor enrichment of Cetuximab incorporated into the liposomes containing 1 mol-% of the cyclic CPP-conjugate, respective liposomes were administered into tumor bearing mice. To obtain these mice, the cell line A431 was injected into Balb/c mice (overexpression of EGFR). The antibody Cetuximab was radiolabeled, incorporated into the liposomes and afterwards applicated orally into the mice. It could be shown a significant increase in the tumor accumulation using the liposomal formulation in comparison with the free peptide (FIG. 23).

Method for the Determination of the Tumor Accumulation of the Antibody Cetuximab.

The animal study was performed according to local authorities using male Wistar rats with a body weight of about 200-250 g. For the determination of the tumor enrichment of Cetuximab, the antibody was radiolabeled with $^{131}$I and incorporated into the liposomal formulation containing 1 mol-% of the cyclic CPP-phospholipid-conjugate and compared with Cetuximab free/i.v. as described previously. At several time points, the tumor enrichment was measured by direct counting of the radiolabeled sample. Briefly, groups (n≥3) of male Wistar rats were formed. Prior to 12 h of the experiment, the rats were kept without food, but with free access to water. Oral application of the liposomes took place by gavage. The blood was removed, weighed and the radioactivity was measured using a Berthold LB 951 G counter in comparison with standards. The blood-associated activity was related to the total injected dose (ID) and expressed as a percentage of the total injected dose per gram of tissue (% ID/g tumor).

Example 18

One further study examined another CPP (MAP) in order to determine the particle characteristics. The conjugates were synthesized and incorporated into the liposomes in a range of 0-1 mol-%. The particle size was similar to standard liposomes and the zeta potential showed an increase demonstrating the successful incorporation of the conjugate into the liposomes (FIG. 24).

Method for Particle Characterization.

The particle size, PDI and zeta potential of all liposomal formulations were determined at room temperature using a Zetasizer Nano ZS from Malvern™ (Malvern Instruments Ltd., Worcestershire, United Kingdom). Size and PDI were measured after dilution to a lipid concentration of 0.076 mg/ml with a 10 mM phosphate buffer with a pH of 7.4 using the automatic mode. The zeta potential was determined after dilution to a lipid concentration of 0.95 mg/ml by a 50 mM phosphate buffer with a pH of 7.4. The default settings of the automatic mode of the Zetasizer Nano ZS from Malvern™ (Malvern Instruments Ltd., Worcestershire, United Kingdom) were the following: number of measurements=3; run duration=10 s; number of runs=10; equilibration time=60 s; refractive index solvent 1.330; refractive index polystyrene cuvette 1.590; viscosity=0.8872 mPa s; temperature=25° C.; dielectric constant=78.5 F/m; backscattering mode (173°); automatic voltage selection; Smoluchowski equation.

CONCLUSION

In this invention a promising novel oral delivery system for a variety of e.g. peptidic drugs such as Vancomycin, Liraglutide, Insulin and antibodies such as Adalimumab or Cetuximab could be established by the use of a variety of the CPP-TEL-liposomes. These results (strongly enhanced mucosal uptake) demonstrate that this novel technology can serve as platform technology for macromolecular drugs (peptides, proteins and antibodies) in general. All CPP-TEL-liposomes showed high homogeneity in size, PDI and incorporation efficiency (>50%). The stability assays in simulated intestinal fluid showed that cyclic CPP-phospholipid-conjugates are more stable than the linear ones, regarding linear CPPs, the incorporation of D-amino acids is preferred. Regarding several linkers differing in the amount of PEG-units, it could be shown that the encapsulation efficiency is higher if PEG-linkers with 8-50 PEG-units are used. To demonstrate that the liposomal characteristics are transferable to other CPPs, the CPP MAP was incorporated into the liposomes which showed characteristics similar to the other CPPs. All liposomal formulations showed no cytotoxicity in all tested concentrations. Furthermore, the long term storage of the CPP-TEL-liposomes could be provided by freeze drying using sucrose as lyoprotector. In the proof of concept study using male Wistar rats (n=6), a 3-fold higher blood concentration of $^{131}$I radiolabeled vancomycin could be detected compared with standard liposomes. In order to confirm these results, the blood concentration was also determined by an immunoassay, which also showed a comparable enrichment of the Vancomycin blood level (7.83% ID vs. 8.68% ID) using the CPP-TEL-liposomal formulation. These results (strongly enhanced mucosal uptake by the liposomal formulations) could be confirmed for further substances such as Liraglutide; Insulin; Adalimumab and Cetuximab by radiolabeling of the substances and determination of radioactivity at determined time points after oral application.

Taken together, the results demonstrate the potential of the CPP-TEL-liposomal formulation according to the present invention for the oral application of all macromolecular drugs as platform technology.

The invention claimed is:

1. A liposomal oral composition comprising liposomes, said liposomes comprising:
   (a) tetraether lipids (TELs), wherein the TEL is selected from the group consisting of glycerylcaldityltetraether (GCTE) and diglyceryltetraether (DGTE) comprising an average number of four to six cyclopentyl rings and TELs comprising three to five pentyl rings, and combinations thereof;
   (b) cell penetrating peptides (CPPs),
      wherein said CPPs are attached to a lipid of the liposome's lipid double layer, and wherein the liposomes have a positive zeta potential and;
   (c) a therapeutic and/or diagnostic agent selected from the group consisting of peptidic macromolecules, proteins and antibodies.

2. The liposomal composition according to claim 1, wherein said TELs are derived from *Sulfolobus* sp.

3. The liposomal composition according to claim 2, wherein said TELs are derived from *Sulfolobus acidocaldarius*.

4. The liposomal composition according to claim 1, wherein said liposomes comprise said TELs in an amount of 1 to 10 mol-% based on the total lipid amount.

5. The liposomal composition according to claim 1, wherein said CPPs are selected from the group consisting of linear or cyclized penetratin (SEQ ID NO: 1), TAT (trans-activator of transcription)-peptide (SEQ ID NO: 2), MAP (model amphipathic peptide) (SEQ ID NO: 3), R9 (SEQ ID NO: 4), pVEC (SEQ ID NO: 5), transportan (SEQ ID NO: 6), and MPG (SEQ ID NO: 7), combinations thereof, and dimers thereof.

6. The liposomal composition according to claim 1, wherein said liposomes comprise said CPPs in an amount of 0.1 to 1 mol-% based on the total lipid amount.

7. The liposomal composition according to claim 1, wherein said compound to which said CPPs are attached is selected from the group consisting of cholesterol and derivatives thereof, phospholipids, lysophospholipids, and tetraetherlipids.

8. The liposomal composition according to claim 1, wherein said CPPs are covalently attached.

9. The liposomal composition according to claim 1, wherein said CPPs are attached via a linker.

10. The liposomal composition according to claim 9, wherein said linker is selected from the group consisting of bifunctional PEG-linkers.

11. The liposomal composition of claim 1, wherein the zeta potential is at least 0.068 mV.

12. The liposomal composition of claim 1, wherein the CPPs are cyclized.

13. The liposomal composition of claim 1, wherein the liposomes have a polydispersity index of at most 0.3.

* * * * *